United States Patent [19]
Collins et al.

[11] Patent Number: 5,240,846
[45] Date of Patent: Aug. 31, 1993

[54] GENE THERAPY VECTOR FOR CYSTIC FIBROSIS

[75] Inventors: Francis S. Collins; James M. Wilson, both of Ann Arbor, Mich.

[73] Assignee: The Regents of the University of Michigan, Ann Arbor, Mich.

[21] Appl. No.: 584,275

[22] Filed: Sep. 18, 1990

Related U.S. Application Data

[63] Continuation-in-part of Ser. No. 401,609, Aug. 31, 1989, which is a continuation-in-part of Ser. No. 399,945, Aug. 24, 1989, abandoned, which is a continuation-in-part of Ser. No. 396,894, Aug. 22, 1989, abandoned.

[51] Int. Cl.⁵ .................... C12P 21/06; C12N 5/00; C12N 15/00; C12Q 1/68
[52] U.S. Cl. ..................... 435/240.1; 435/172.3; 435/6; 435/69.1; 435/29
[58] Field of Search ............. 435/240.2, 172.3, 69.1, 435/320.1, 236, 235.1; 536/27; 935/32, 34, 57

[56] References Cited

U.S. PATENT DOCUMENTS

| | | | |
|---|---|---|---|
| 4,844,893 | 7/1989 | Honsky et al. | 424/85.8 |
| 4,847,201 | 7/1989 | Kaswasaki et al. | 435/70 |
| 4,853,331 | 8/1989 | Hernstadt et al. | 435/252.1 |
| 4,861,589 | 8/1989 | Ju | 424/93 |
| 4,861,719 | 8/1989 | Miller | 435/236 |
| 4,868,116 | 9/1989 | Morgan et al. | 435/240.2 |
| 4,980,286 | 12/1990 | Morgan et al. | 435/172.3 |

FOREIGN PATENT DOCUMENTS 2203742  4/1987  United Kingdom .

OTHER PUBLICATIONS

Jetten et al. Science 244:1472 1989.
Boat et al., "Human Respiratory Tract Secretions", Arch. Biochem. Biophys. 177, 95-104 (1976).
Boucher et al., "Na⁻ Transport In Cystic Fibrosis Respiratory Epithelia", J. Clin. Invest. 78, 1245-1252 (1986).
Cheng et al., "Increased Sulfation Of Glycoconjugates By Cultured Nasal Epithelial Cells From Patients With Cystic Fibrosis", J. Clin. Invest. 84, 68-72 (1989).
Cliff et al., "Separte Cl⁻ Conductances Activated By cAMP and Ca²⁺ in Cl⁻-Secreting Epithelial Cells", PNAS (USA) 87, 4956-4960 (1990).
Collie et al., "Culture Of Sweat Gland Epithelial Cells From Normal Individuals And Patients With Cystic Fibrosis", In Vitro Cell & Devl. Biol. 21, 597-602 (1985).
Collins et al., "Construction Of A General human Chromosome Jumping Library, With Application To Cystic Fibrosis", Science 235, 1046-1049 (1987).
Cutting et al., "A Cluster Of Cystic Fibrosis Mutations In The First Nucleotide-Binding Fold Of The Cystic Fibrosis Conductance Regulation Protein", Nature 346, 366-368 (1990).
Dean et al., "Multiple Mutations In Highly Conserved Residues Are Found In Mildly Affected Cystic Fibrosis Patients", Cell 61, 863-870 (1990).
Drumm et al., "Physical Mapping Of The Crystic Fibrosis Region By Pulsed-Field Gel Electrophoresis", Genomics 2, 346-354 (1988).
Fienberg et al., "A Technique For Radiolabeling DNA Restriction Endonuclease Fragments To High Specific Activity", Anal. Biochem. 132, 6-13 (1983).

(List continued on next page.)

Primary Examiner—Robert A. Wax
Assistant Examiner—Michel Escallen
Attorney, Agent, or Firm—Harness, Dickey & Pierce

[57] ABSTRACT

The present invention comprises gene therapy for treating cystic fibrosis(CF). Delivery and expression of a single copy of a normal CFTR gene leads to stable correction of the Cl channel regulation defect present in CF epithelial cells. The present invention includes recombinant viral and plasmid vectors, alternative CFTR gene delivery strategies, and transduced CF cells and cell lines carrying a recombinant gene for functional CFTR. CF epithelial complementation through transduction of the present invention also provides an assay for determining the validity of other putative CF mutations.

16 Claims, 8 Drawing Sheets

OTHER PUBLICATIONS

Frizzell et al., "Cystic Fibrosis: A Disease Of Ion Channels?", *Trends Neurosci* 10, 190–193 (1987).

Frizzell et al., "Altered Regulation Of Airway Epithelial Cell Chloride Channels In Cystic Fibrosis", *Science* 233, 558–560 (1986).

Green et al., "Chromosomal Region Of The Cystic Fibrosis Gene In The Yeast Artificial Chromosomes: A Model For Human Genome Mapping", *Science* 250, 94–98 (1990).

Harris et al., "Establishment Of A Tissue Culture System For Epithelial Cells Desired From Human Pancreas: A Model For The Study Of Cystic Fibrosis", *Cell* 87, 695–703 (1987).

Hyde et al., "Structural Model For ATP-Binding Proteins Associated With Cystic Fibrosis, Multidrug Resistance And Bacterial Transport", *Nature* 346, 362–365 (1990).

Kerem et al., "Identification Of The Cystic Fibrosis Gene: Genetic Analysis", *Science* 245, 1073–1080 (1989).

Kerem et al., "Another Signel Amino Acid Deletion In The Putative ATP-Binding Domain Of The Cystic Fibrosis Gene Product", *PNAS (USA)* 87, 8447–8451 (1990).

Korman et al., "Expression Of Human Class II Major Histocompatibility Complex Antigens Using Retrovirus Vectors", *PNAS (USA)* 84, 2150–2154 (1987).

Li et al., "Cyclic AMP-Dependent Protein Kinase Opens Chloride Channels In Normal But Not Cystic Fibrosis Airay Epithelium", *Nature* 331, 358–360 (1988).

Quinton et al., "Cystic Fibrosis: A Disease In Electrolyte Transport", *FASEB J.* 4, 2709–2717 (1990).

Riordan et al., "Identification Of The Cystic Fibrosis Gene: Cloning and Characterization of Complementary DNA", *Science* 245, 1066–1073 (1989).

Riordan et al., *Genetics And Epithelial Cell Dysfunction In Cystic Fibrosis*, 59–71 (1987).

Rommens et al., "Identification Of The Cystic Fibrosis Gene: Chromosome Walking And Jumping", *Science* 245, 1059–1065 (1989).

Sanbrook et al, "Oligonucleotide-Mediated Mutagenesis", *Molecular Cloning. A Laboratory Manual* 2nd Ed., Cold Spring Harbor Press, 15.51–15.80 (1989).

Sato et al., "Defective Beta Adrenergic Response Of Cystic Fibrosis Sweat Glands In Vivo And In Vitro", *J. Clin. Invest.* 73, 1763–1771 (1984).

Schoumacher et al., "A Cystic Fibrosis Pancreatic Adenocarcinoma Cell Line", *PNAS (USA)* 87, 4012–4016 (1990).

Smith et al., "In Vitro Mutagenesis", *Annu. Re. Genet.* 19, 423–462 (1985).

Stutts et al., "Chloride Uptake Into Cultured Airway Epithelial Cells From Cystic Fibrosis Patients And Normal Individuals", *PNAS (USA)* 82, 6677–6681 (1985).

Taussig et al., "Cystic Fibrosis: An Overview", *In Cystic Fibrosis,* L. M. Taussig, ed. New York: Thieme-Stralton 1–9 (1984).

Tsui et al., "Cystic Fibrosis Locus Defined By A Genetically Linked Polymorphic DNA Marker", *Science* 230, 1054–1057 (1985).

Venglarik et al., "A Simple Assay For Agonist-Regulated Cl and K Conductances In Salt-Secreting Epithelial Cells", *Am. J. Physiol.* 259, C358–C364 (1990).

Welsh et al., "Abnormal Regulation Of Ion Channels In Cystic Fibrosis Epithelia", *FASEB J.* 4, 2718–2725 (1990).

Welsh et al., "Chloride And Potassium Channels In Cystic Fibrosis Airway Epithelia", *Nature* 322, 467–470 (1986).

White et al., "A Frame-Shift Mutation In The Cystic Fibrosis Gene", *Nature* 344, 655–667 (1990).

Willumsen et al., "Activation Of An Apical Cl$^-$ Conductance By Ca$^{2+}$ Ionphores In Cystic Fibrosis Airway Epithelia", *Am. J. Physiol.* 256, C226–C233 (1989).

Wilson et al., "Correction Of CD18-Deficient Lymphocytes By Retrovirus-Mediated Gene Transfer", *Science* 248, 1413–1416 (1990).

Wilson et al., "Correction of The Genetic Defect In Hepatocytes From The Watanabe Heritable Hyperlipidemic Rabbit", *PNAS (USA)* 85, 4421–4425 (1988).

Wilson et al., "Expression Of Human Adenosine Deaminase In Mice Reconstituted With Retrovirus-Transduced Hematopoietic Stem Cells", *PNAS (USA)* 87, 439–443 (1990).

"The Cystic Fibrosis Genetic Analysis Consortium", *Am. J. Hum. Genet.* 47:354–359 (1990).

Schoumacher et al., "Phosphorylation Fails To Activate Chloride Channels From Cystic Fibrosis Airway Cells", *Nature* 330, 752–754 (1987).

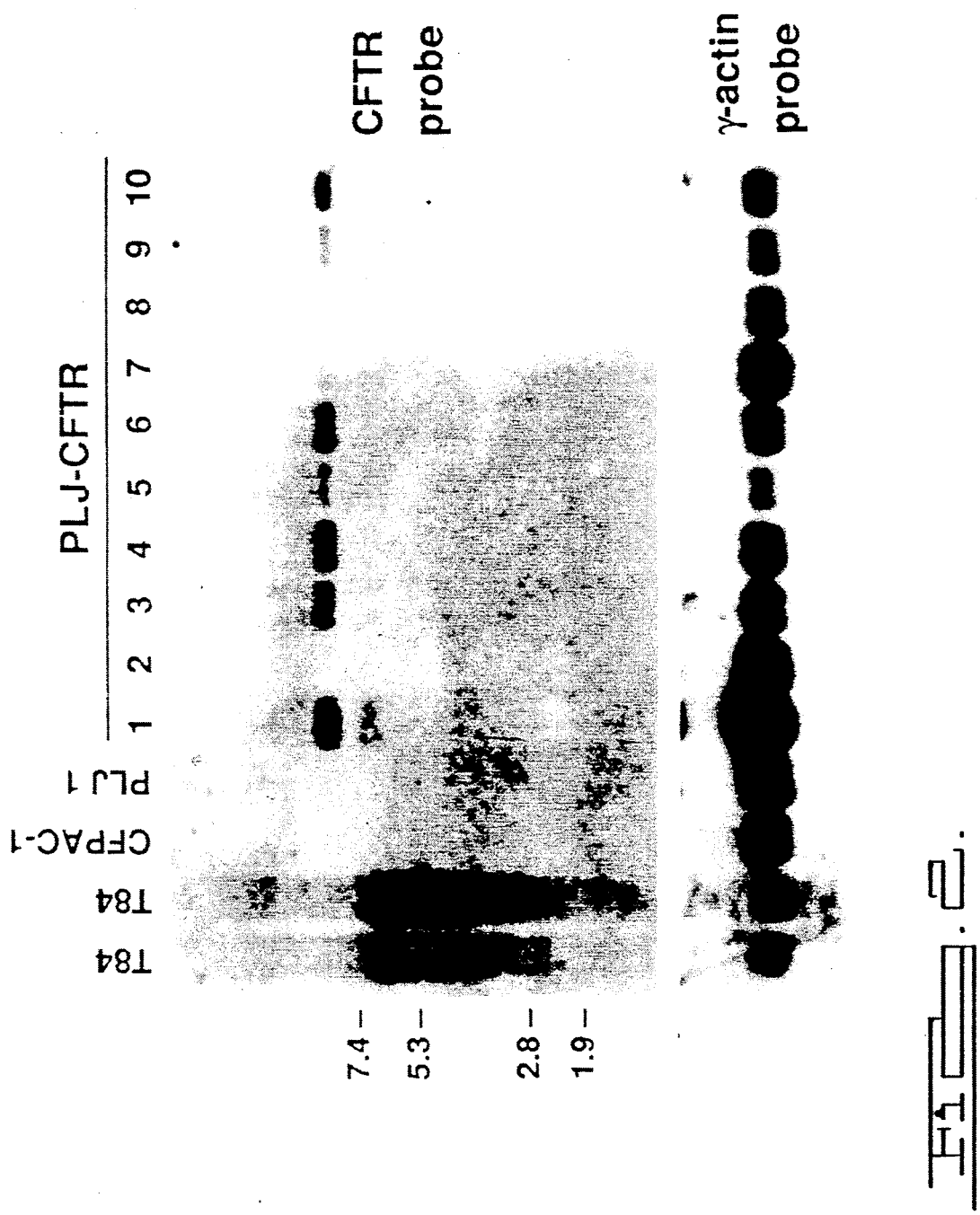

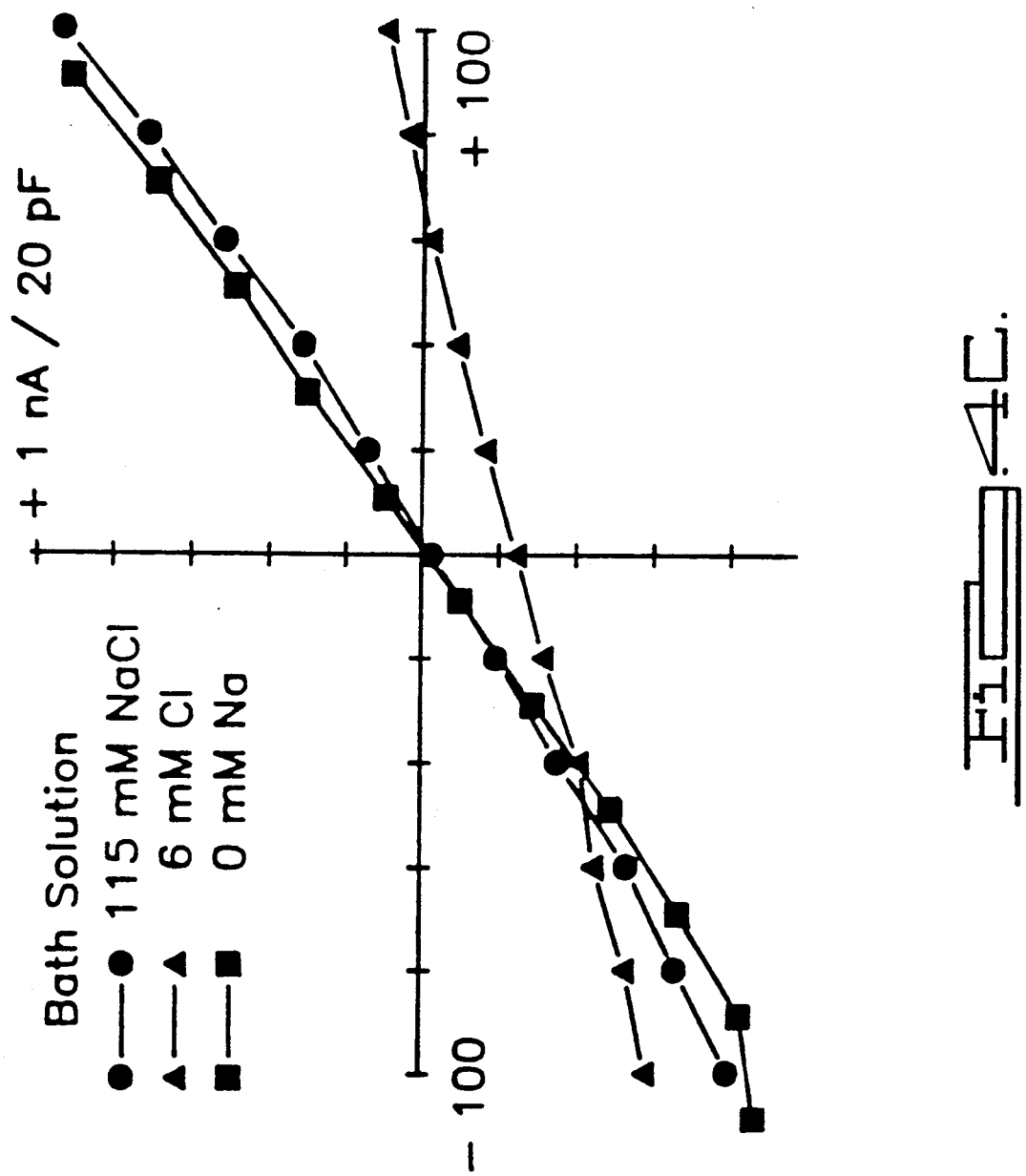

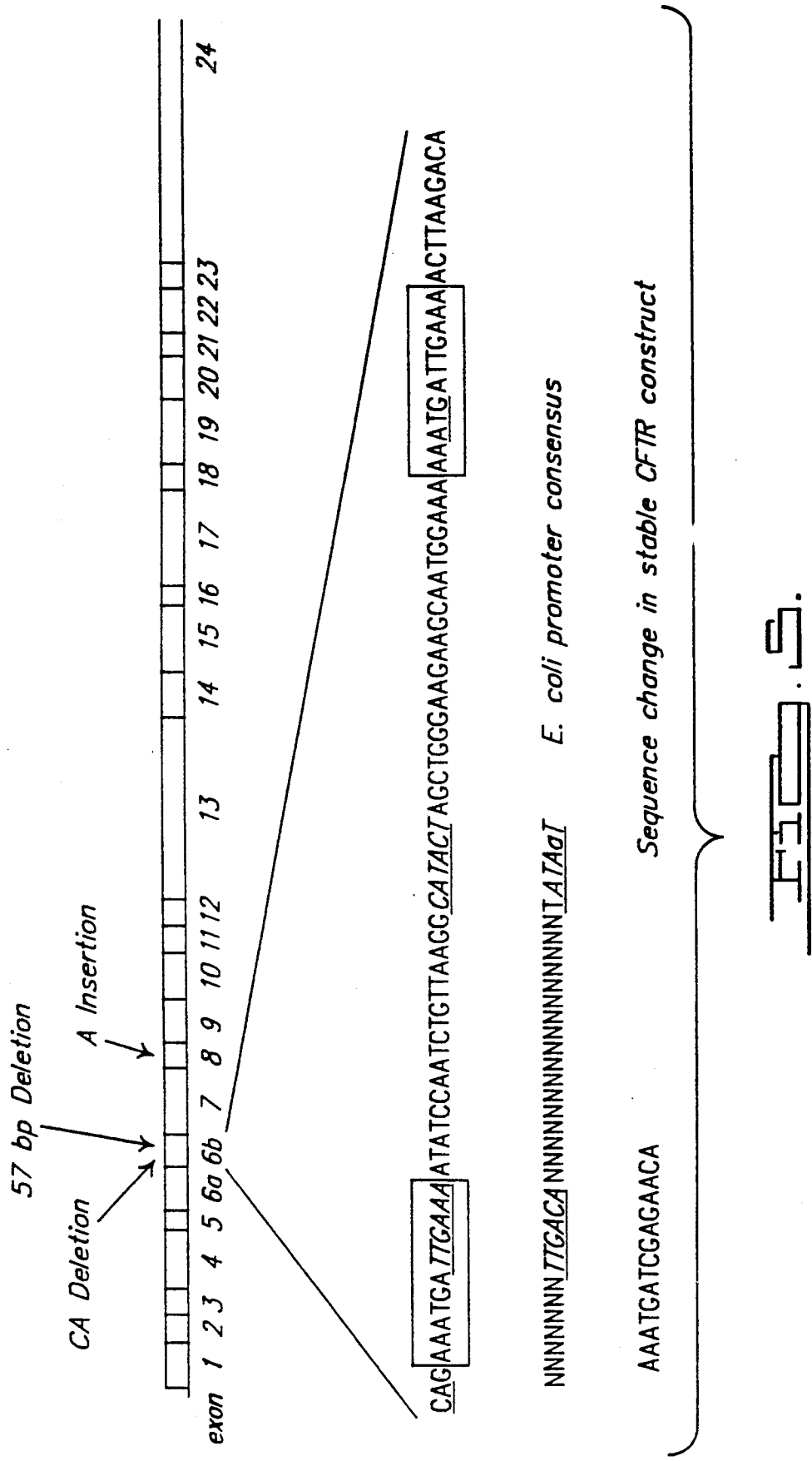

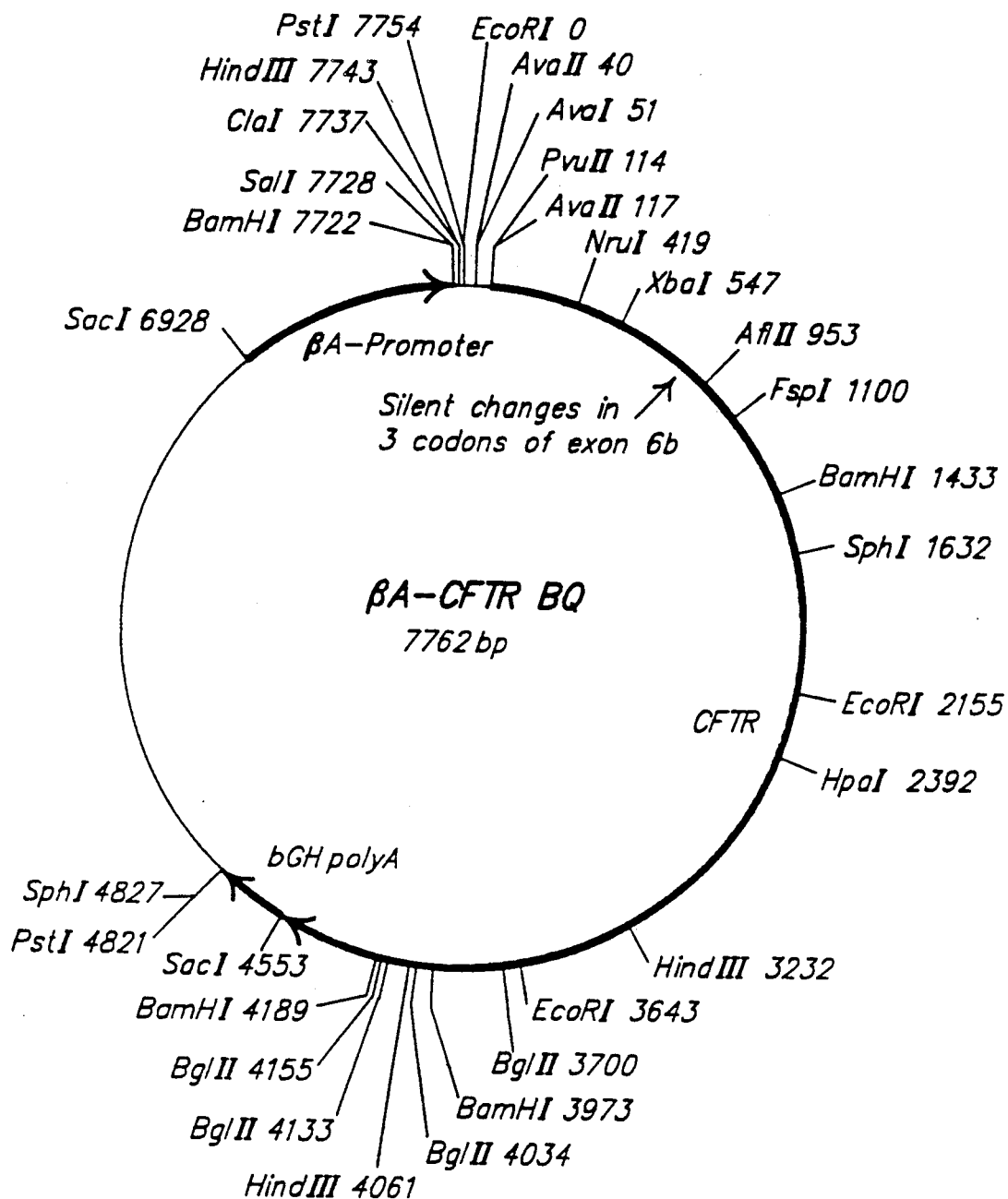

GENE THERAPY VECTOR FOR CYSTIC FIBROSIS

SPONSORSHIP

Work on this invention was supported by the Cystic Fibrosis Foundation and by the United States government under grants DK42718 and DK39690 awarded by the National Institute of Health. The government has certain rights in the invention.

RELATED APPLICATIONS

This application is a continuation-in-part of U.S. application Ser. No. 401,609, entitled "Cystic Fibrosis Gene", filed on Aug. 31, 1989, which is a continuation-in-part of U.S. application Ser. No. 399,945, entitled "Cystic Fibrosis Gene", filed on Aug. 24, 1989, now abandoned, which is a continuation-in-part of U.S. application Ser. No. 396,894, entitled "Cystic Fibrosis Gene", filed on Aug. 22, 1989, now abandoned, all of which applications are specifically incorporated by reference herein.

FIELD OF THE INVENTION

The present invention relates generally to gene therapy for cystic fibrosis (CF) and, more particularly, to transfer of the gene for cystic fibrosis transmembrane conductance regulator (CFTR) to correct the defect in epithelial cell Cl channel regulation in cystic fibrosis patients.

BACKGROUND OF THE INVENTION

Cystic fibrosis (CF) is an autosomal recessive disorder characterized by abnormalities in water and electrolyte transport that lead to pancreatic and pulmonary insufficiency. Taussig, L. M., An overview. In Cystic Fibrosis. L. M. Taussig, ed. (New York: Thieme-Stralton). 1-9 (1984). It is one of the most common severe autosomal recessive disorders, having a 5% carrier frequency and affecting about 1 in 2500 live births in North America.

Functional expression of the CF defect reduces the chloride ion permeability of epithelial tissues. Quinton, P. M., Faseb J. 4, 2709-2717 (1990). The ability of epithelial cells in the airways, sweat glands, pancreas and other tissues to secrete Cl in response to cAMP-mediated agonists is most or severely reduced. Activation of apical membrane Cl channels by cAMP-dependent protein dinase (PKA) is impaired, but channels with normal conductance properties can be activated by other means, including agonists whose effects are mediated by increased cell Ca. Frizzell, R. A. et al., Trends Neurosci, 10, 190-194 (1987); Welsh, M. J., FASEB J. 4, 2718-2725 (1990). These finds suggest that the Cl channel per se is not defective in CF, but that the defect might lie in a regulatory protein that transduces the effects of protein kinase activation. The presence of abnormalities in epithelial sodium transport in CF cells further supports the concept of a regulatory defect that can affect other cellular functions. Boucher, R. C. et al., J. Clin. Invest. 78, 1245-1252 (1986).

Isolation of the gene for CF, as described in detail in the aforementioned related applications has provided further insight into the molecular basis of the disease. See also Rommens, J. M. et al., Science 245, 1059-1065 (1989); Riordan, J. R. et al., Science 245, 1066-1073 (2989); Derem, B. S. et al., Science 245, 1073-1080 (1989). The gene responsible for CF has been localized to 250,000 bp of genomic DNA based on its location within the genome. This gene encodes a protein of 1480 amino acids called the cystic fibrosis transmembrane conductance regulator (CFTR). Riordan et al., supra.

The most compelling evidence thus far to support the role of CFTR in the etiology of CF has been provided by genetic analyses. Kerem et al., supra, (1989). Sequence analysis of the CFTR gene of CF chromosomes has revealed a variety of mutations, including nonsense and frameshift mutations. Cutting, G. R. et al., Nature 346, 366-369 (1990); White, M. B. et al., Nature 344, 655-667 (1990); Dean, M. et al., Cell 16, 863-870 (1990); Kerem, B. S. et al., identification of mutations in regions corresponding to the 2 putative nucleotide (ATP) binding folds of the cystic fibrosis gene, PNAS (USA) (1990) (in press). However, extensive population studies have indicated that the most common CF mutation is a deletion of the three nucleotides that encode phenylalanine 508 ($\Delta F_{508}$). This deletion is present on 70% of all CF chromosomes, but not on normal chromosomes. Kerem et al., supra (1989); The Cystic Fibrosis Genetic Analysis Consortium (1990).

Results from both physiological and molecular cloning studies have raised the possibility that CFTR is a Cl channel. The defect in Cl channel activation by cAMP-dependent protein kinase (PKA) is present at the single-channel level in cell-free membrane patches and the protein structure predicted from CF gene closing suggests that CFTR is an integral membrane protein with twelve membrane-spanning domains. Schoumacher, R. A. et al., Nature 330, 152-754 (1987); Li, M. et al., Nature 331, 358-360 (1988); Riordan et al., supra. The identification of CF-associated alterations in other cellular processes such as amiloride-sensitive Na transport and mucin sulfation also supports the view that CFTR may regulate several cellular processes. Boucher et al., supra; Boat, T. F. et al; Arch. Biochem. Biophys. 17, 95-104 (1976).

Although the specific role that CFTR plays in Cl transport remains to be determined, the CFTR protein contains several interesting functional domains including two nucleotide binding folds, a regulatory region that has many possible sites for phosphorylation, and two hydrophobic regions that probably interacted with cell membranes. CFTR shows structural similarity with several members of the "ATP binding cassette" (ABC) superfamily of proteins, including the periplasmic binding proteins of prokaryotes, and the P-glycoprotein associated with multidrug resistance in higher eudaryotes. Riordan et al., supra; Hyde, S. C. et al., Nature 346, 312-365 (1990).

Recent progress in our understanding of the genetic and functional basis of CF has provided a foundation for better defining its molecular pathology as well as developing novel therapies based on somatic gene transfer.

SUMMARY OF THE INVENTION

Gene therapy for cystic fibrosis (CF) comprises the delivery of a gene for functional cystic fibrosis transmembrane conductance regulator (CFTR) to affected epithelial cells. Delivery and expression of a single copy of the normal CFTR gene, as would be expected with a recessive trait such as CF, alleviates the Cl channel regulation defect present in CF cells. CF caused by a lack of functional CFTR or presence of CFTR function below physiologically-acceptable levels which arises from a defect in the CFTR gene can thus be treated in accordance with the principles of the present invention.

The "normal CFTR gene" of the present invention is simply any nucleic acid sequence which codes for functional CFTR. Thus variations in the actual sequence of the gene can be tolerated provided that functional CFTR can be expressed. For example, silent mutations can be introduced to stabilize cloning of the gene. A CFTR gene used in the practice of the present invention can be obtained through conventional methods such as DNA cloning, artificial construction or other means. The 4.6 kb cNDA utilized in the specific examples has all the sequences necessary to encode for a functional CFTR protein, as assayed by the analysis of cAMP-stimulated chloride current.

Gene transfer of the CFTR gene in accordance with the present invention can be accomplished through many means, including transfection using calcium phosphate coprecipitation, fusion of the target cell with liposomes, erythrocyte ghosts or spheroplasts carrying the CFTR gene, plasmid and viral vector-mediated transfer and DNA protein complex-mediated gene transfer.

Presently the delivery vehicle of choice is a recombinant retrovirus capable of infecting human epithelial cells. This is somewhat surprising given the relatively large size of the CFTR gene. The recombinant retroviral vector of the invention generally comprises DNA of at least the portion of the retroviral genome necessary for infection, and the normal CFTR gene operatively linked thereto. Additionally, the portion of retroviral genome used in construction of the vector can be rendered replication-defective to remove any deleterious effects of viral replication on the target cells.

Although any CF-affected epithelial cells such as pancreatic and sweat gland cells can be targeted with the gene transfer methods and vectors of the present invention, because the most severe complications of CF are usually pulmonary, airway epithelial cells are the most desirable targets for gene therapy of the present invention. Moreover, given that airway epithelial cells have been found to be easily infected by recombinant retroviruses, gene transfer in accordance with the present invention to these cells is quite feasible.

CF diagnosis and screening of carriers can also be accomplished through transduction of CFTR defective cells and cell lines. For example, the complementation scheme of the present invention can be use to determine the validity of other putative CF mutations and is also useful as a tool to study the function of CFTR by site-specific mutagenesis or domain switching with other members of this large ABC gene family.

The present invention is thus directed towards gene therapy for cystic fibrosis through delivery and expression of a functional CFTR gene to the cells of a CF patient. Recombinant retroviral vectors as well as other CFTR gene transfer schemes can be used in the practice of the present invention. The present invention further includes both CF epithelial cells and cell lines which carry a normal CFTR gene transducted or transferred therein in accordance with the principles of the invention. CFTR screening and complementation assays for other putative CF mutations are also contemplated within the scope of the present invention.

BRIEF DESCRIPTION OF THE DRAWINGS

FIG. 2 is an RNA blot analysis of the expression of the retroviral transduced CFTR gene in CFPAC clones using the CFTR exon 13 probe. Clones of retrovirus transduced CFPAC-1 cells were isolated and analyzed for the presence of CFTR transcripts. Total cellular RNA was harvested from individual clones and subjected to RNA blot analysis using the exon 13 CFTR probe to hybridize with the filter (top panel). The filter was stripped and rehybridized with a probe derived from human $\gamma$-acetin cDNA (bottom panel) in order to control for variation in sample loading. RNA samples (10 $\mu$g) were derived from the following cells: lanes "T84" - duplicate samples from the colonic tumor cell line T84; lane "CFPAC-1" - nontransduced CFPAC-1 cells; lane "pLJ 6"-CFPAC-1 clone #6 from the pLJ infection; and lanes "pLJ-CFTR 1 to 10" - CFPAC-1 clones #1 through #10 from the pLJ-CFTR infection. Molecular size markers in kilobases are noted along the left border.

FIG. 4C is a graph depicting the instantaneous current-voltage relations of forskolin-induced currents in NaCl, low CL and Na-free baths. Forskolin-induced currents were obtained by digital subtraction of currents before and after stimulation; the values shown were recorded 6 msec after the initiation of voltage pulses. These data were obtained from the pLJ-CFTR clone 6 cell record shown in FIG. 4A during the 6 min. recording gap.

FIG. 5 depicts a stabilization scheme for a CFTR construct.

FIG. 6 is a restriction map of a plasmid-based vector used in the practice of the present invention.

DESCRIPTION OF SEQUENCE LISTING

Figure 1A:
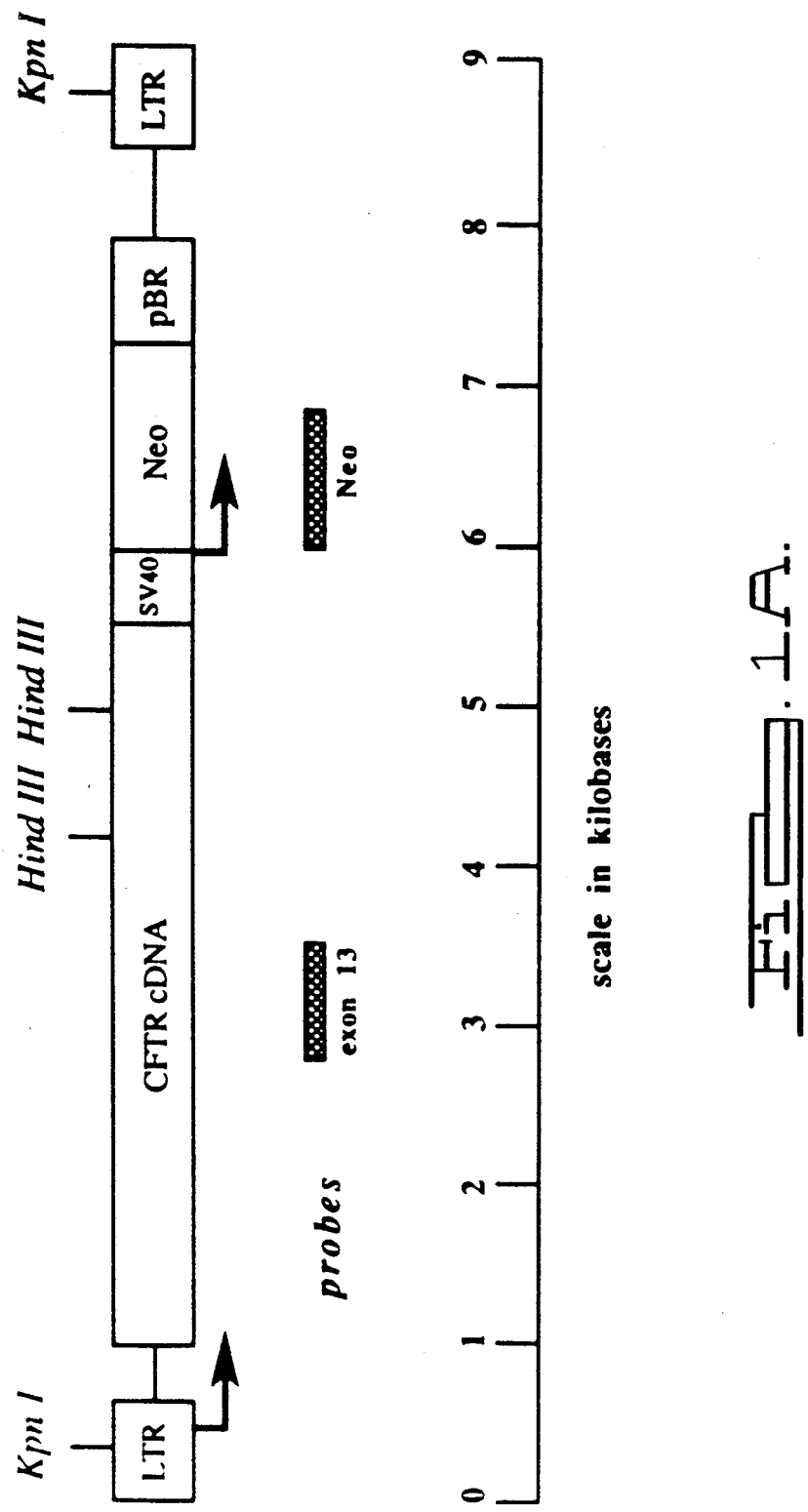
FIG. 1A depicts the proviral component of the recombinant retroviral vector pLF-CFTR of the present invention. Important structural components of the vector include the long-terminal repeat sequences (LTR), CFTR cDNA, sequences from the origin of SV40, the gene that confers resistance to G418(Neo), and the origin of replication for pBR322(pBR). Sites of transcriptional initiation are indicated with arrows at the 5'LTR and the internal SV40 sequences. Recognition sites for restriction endonucleases Kpn I and Hind III are indicated. Probes specific for the CFTR gene (exon 13) and the Neo gene that were used in DNA and RNA blot analysis are indicated below the vector.

The Sequence Listing at the end of the Specification is the nucleotide sequence of cDNA encoding CFTR together with the deduced amino acid sequence. DNA sequencing was performed by the dideoxy-chain termination method with $^{35}$S-labeled nucleotides or by the Dupont Genesis 2000 automatic DNA sequencer. Numbers on the right of the columns indicate base positions. The first base position corresponds to the first nucleotide in the 5' extension clone PA3-5, which is one nucleotide longer than TB2-7. The 3' end and the noncoding sequence are shown above [nucleotides 4561 to 6129 plus the poly(A)+tail]. Arrows indicate position of transcription initiation site by primer extension analysis. Nucleotide 6129 is followed by a poly(A) tract. Positions of exon junctions are indicated by vertical lines. Potential membrane-spanning segments ascertained with the use of the algorithm of Eisenbert et al., *J. Mol. Biol.* 179, 125 (1984) are boxed. Glycosylation sites are designated with a +. Amino acids comprising putative ATP-binding folds are underlined. Possible sites of phosphorylation by protein kinases A or C are indicated by o and *, respectively. The open triangle indicates the position at which 3 bp are deleted in CF. Abbreviations for the amino acids residues are: A, Ala; C, Cys; D, Asp; E, Glu;F, Phe, G, Gly; H, His; Ile; K, Kys; L, Leu; M, Met; N, Asn; P, Pro; Q, Gln; R, Arg; S, Ser; T, Thr; V, Val; W, Trp; and Y, Try.

DETAILED DESCRIPTION OF THE PREFERRED EMBODIMENTS OF THE INVENTION

The absence of functional CFTR or CFTR function which is not at physiologically-acceptable levels and which arises from a defect in the CFTR gene is treated through gene transfer of a normal CFTR gene into CFTR defective cells. By "physiologically-acceptable level of CFTR function" is meant a level of CFTR function at which a cell population or patient exhibits the normal physiological effects presence of the normal amounts of CFTR. Examples of insufficiencies in CFTR function include but are not limited to abnormal Cl channel regulation in epithelial cells, such as that exhibited in cystic fibrosis.

A recombinant viral vector of the present invention comprises DNA of at least a portion of retroviral genome which portion is capable of infecting the target cells and a normal CFTR gene operatively linked to thereto. By "infection" is generally meant the process by which a virus transfers genetic material to its host or target cell. Preferably the retrovirus used in the construction of a vector of the invention is also rendered replication-defective to remove the effects of viral replication on the target cells. In such cases, the replication-defective viral genome can be packaged by a helper virus in accordance with conventional techniques. Generally any retrovirus meeting the above criteria of infectiousness and capabilities of CFTR gene transfer can be employed in the practice of the present invention may also be desirable. Suitable retroviruses for the practice of this invention include, for example, pLJ, pZip, pWe and pEM well known to those skilled in the art. suitable packaging virus lines for replication-defective retroviruses include, for example, ΨCrip, ΨCre and Ψ2 and ΨAm.

It will be appreciated that when viral vector schemes are employed for CFTR transfer, the use of attenuated or a virulent virus may also be desirable. Where applicable in the practice of the invention, amplification of the CFTR gene can also be utilized to enhance the levels of normal CFTR expression.

The genetic material to be recombined with the retroviral vector or transferred through other methods of the invention is preferably provided through conventional cloning methods, i.e. cDNA, through overlapping oligonucleotide sequences or any other suitable method yielding the desired sequence. When used in diagnostic or screening assays, the genetic material is usually provided by cloning of patient DNA or, alternatively, through the use of patient genomic DNA. As stated previously, by normal CFTR gene, is meant any nucleic acid sequence which codes for functional CFTR.

The cells targeted for transduction or gene transfer in accordance with the present invention include any cells to which the delivery of the CFTR gene is desired. Generally speaking, the cells are those with the CFTR gene defect, such as CF cells. In the case of CF, the cells targeted are preferably epithelial cells, including pancreatic, sweat gland, liver, intestinal, kidney and even more preferably epithelial airway cells, such as lung cells.

Cells or cell populations can be treated in accordance with the present invention in vivo or in in vitro. For example, in in vivo treatments, CFTR vectors of the present invention can be administered to the patient, preferably in a biologically compatible solution or pharmaceutically acceptable delivery vehicle, by ingestion, injection, inhalation or any number of other methods. The dosages administered will vary from patient to patient and will be determined by the level of enhancement of CFTR function balanced against any risk or deleterious side effects. Monitoring levels of transduction, CFTR expression and/or the presence or levels of normal CFTR will assist in selecting and adjusting the dosages administered. In vitro transduction is also contemplated within the present invention. Cell populations with defective CFTR genes can be removed from the patient or otherwise provided, transduced with a normal CFTR gene in accordance with the principles of the invention, then (re)introduced into the patient.

CFTR-defective cell lines, such as transformed CF lines, can also be transduced in accordance with the present invention. Such cell lines are useful, for example, in complementation assays for evaluating CF mutations to diagnose CF and screen for carriers. For example, patient CFTR cDNA can be transferred into CF cells and the cells screened for complementation, i.e. CFTR function, to confirm or rule out of CF or CFTR gene defects.

In the first set of Specific Examples which follow, retrovirus-mediated gene transfer was used to complement the cystic fibrosis (CF) defect in Cl regulation in epithelial cells of a CF patient. Amphotropic retroviruses were used to transduce a functional cystic fibrosis transmembrane conductance regulator (CFTR) cDNA into CFPAC-1, a pancreatic adenocarcinoma cell line derived from a patient with CF. This cell line stably expresses abnormalities in electrolyte transport that are characteristic of the CF defect, i.e. they lack cAMP-stimulated Cl transport. CFPAC-1 cells were exposed to control virus (pLJ) and CFTR-expressing virus (pLJ-CFTR); viral transduced clones were isolated and subjected to molecular and physiologic analysis. Agarose gel blot analysis revealed unrearranged proviral sequences in 10 of 10 pLJ clones and 9 of 10 pLJ-CFTR clones. RNA analysis detected a viral-derived CFTR transcript in all of the pLH-CFTR clones. RNA analysis detected a viral-derived CFTR transcript in all of the pLJ-CFTR clones that contained unrearranged proviral sequences.

Anion ($^{125}$) efflux was used to examine pLJ and pLJ-CFTR clones for cAMP and Ca stimulated anion transport. Agents that increase intracellular cAMP stimulated $^{125}$I efflux in pLJ-CFTR clones but not pLJ clones. While-cell patch-clamp performed on two responding clones showed that the anion efflux responses wee due to cAMP stimulation of chloride conductance. Calcium ionophore increased $^{125}$I efflux and chloride currents in all pLJ and PLJ-CRFT clones. These findings indicate that expression of the normal CFTR gene confers cAMP-dependent Cl channel regulation on CF epithelial cells.

The second set of Specific Examples describes gene transfer to airway epithelial cells as well as pancreatic cells, administration of CFTR gene therapy and alternative gene transfer delivery system, including lipofection and DNA-protein complex-mediated gene transfer.

SPECIFIC EXAMPLE - I

Recombinant Retroviruses

Early attempts to reconstitute a full length CFTR cDNA from overlapping clones were unsuccessful. The exact cause of these difficulties remains to be defined, but our data indicated that prokaryotic transcription from internal CFTR cDNA sequences may result in the expression of a protein that is toxic to bacteria. The introduction of three silent mutations. (T to C at 930, A to G at 933, and T to C at 936) into a restriction fragment of CFTR that spans exon 6b completely ablated this toxic effect, potentially by interfering with the cryptic prokaryotic promoter, and enabled the reconstruction of 4.6 kb of contiguous CFTR cDNA sequence. The nucleotide sequence of this reconstructed cDNA was re-determined and found identical to that published previously with the exception of the three silent mutations noted above. See Sequence Listing and Riordan et al., supra.

The modified CFTR cDNA was cloned into the retroviral vector pLJ previously described by Korman, A. J. et al., PNAS (USA) 84, 2150-2154 (1987). The proviral component of this recombinant vector, called pLJ-CFTR, is depicted in FIG. 1A. Transcription from the 5'LTR produces and 8.5 kb genomic transcript that is responsible for viral passage and CFTR expression. Transcripton from SV40 sequences located internal to the LTRs leads to the formation of a second transcriptional unit that expresses a Neo-selectable marker.

Transfection of pLJ and PLJ-CFTR vectors into the virus packaging cell line ΨCrip led to the transient production of replication-defective virus. Limiting dilutions of virus stocks were used to infect CFPAC-1 cells which were subsequently cultured in the presence of G418 in order to select for transduced clones. Transiently produced pLJ-CFTR virus stocks had a lower titer (50-100 fold) than those produced with pLJ vector. Ten individual clones of cells were isolated from infections performed with each type of virus (named pLJ clones 1 through 10 and pLJ-CFTR clones 1 through 10) and subjected to molecular and physiologic analysis.

Transduced Clones Express Retroviral CFTR Sequences

Retrovirally transduced clones of CFPAC-1 cells were analyzed for proviral sequences as described for other cells types by Wilson, J. M. et al., PNAS (USA) 85, 4421-4425 (1988) and Wilson, J. M. et al., Science 248, 1413-1416(1990). Digestion of high molecular weight DNA with restriction enzyme Kpn I, which has unique sites in the vector LTRs, releases all integrated forms of the PLJ-CFTR provirus as a common 8.5 kb fragment. As shown in the top panel of FIG. 1B, gel blot hybridization of Kpn I-restricted DNA revealed unrearranged proviral sequences with the expected abundance of one copy per cell in 10/10 pLJ clones and 9/10 PLJ-CFTR clones. Hybridization of the filter with a Neo-specific probe detected a markedly rearranged provirus in pLJ-CFTR clone 2; this virus apparently deleted a major part of the CFTR cDNA (data now shown).

Gel blot hybridization analysis was also used to study the complexity and uniqueness of each putative pLJ-CFTR clone. High molecular weight DNA was digested with Hind III, a restriction enzyme with two internal sites in pLJ-CFTR, and analyzed with the exon 13 CFTR specific probe, with the results shown in the bottom panel of FIG. 1B. This analysis demonstrated the existence of a single unique integration site in 9/10 pLJ-CFTR clones. The CFTR specific probe failed to detect the provirus in DNA form pLJ-CFTR clone 2 because of the apparent deletion described above.

Expression of the retroviral transduced CFTR gene was studied by RNA blot analysis using the CFTR exon 13 probe and is shown in FIG. 2. Total cellular RNA from the previously described human colon tumor cell line, T84, demonstrated high levels of the endogenous CFTR transcript. No CFTR transcript was detected by Northern analysis in mock infected CFPAC-1 cells or pLJ clones 1 through 10 CFTR RNA can be detected in CFPAC-1 by RNA-PCR. A viral directed CFTR transcript of the expected size (i.e., 8.5 kb) was detected in 9/10 pLJ-CFTR clones; the CFTR probe failed to detect a transcript in RNA from the clone that contains the deleted provirus (pLJ-CFTR clone 2).

Transduced Clones Show Forskolin Stimulation of Anion Transport

Figure 3A:
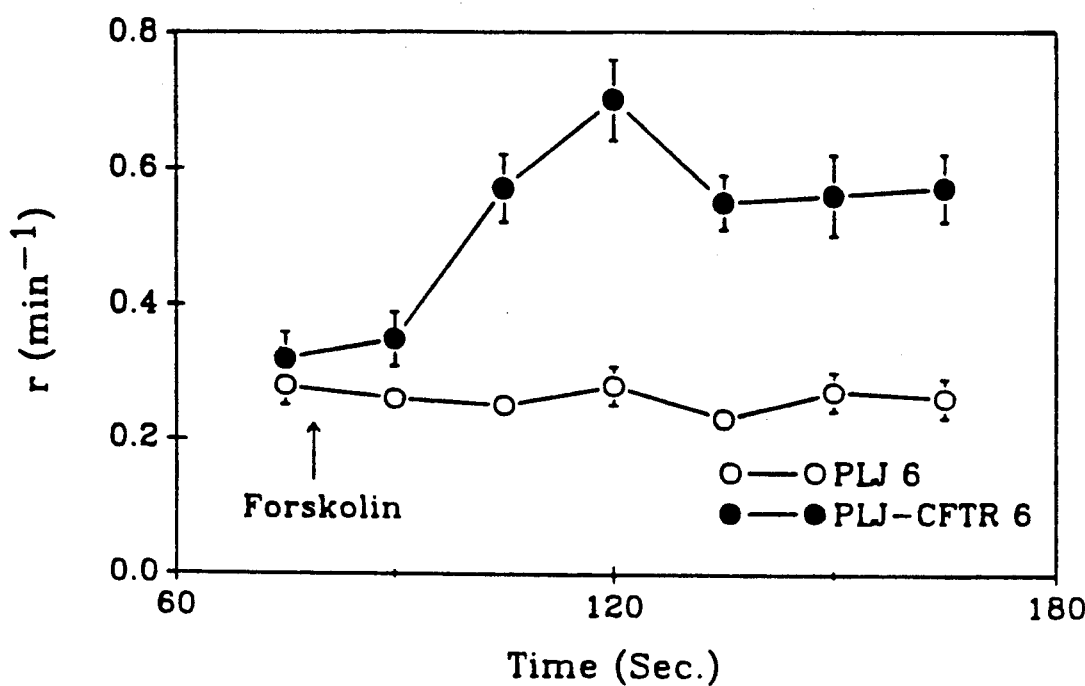
FIG. 3A is a graph illustrating the effect of forskolin on $^{125}$I efflux in pLJ and pLJ-CFTR clones over time. The time course of the efflux rae constant in clones 6 is shown. Forskolin (10 $\mu$M) was added att he indicated time. The first 60 sec of efflux allows for washout of extracellular $^{125}$I and is not shown (see Experimental Protocol set forth below). Mean +/−SEM; n=9 for all clones except pLG 5 where n=7.

Isotopic anion ($^{125}I$) effluxes were measured to screen the pLJ and pLJ-CFTR clones for cAMP- and Ca-stimulated anion transport. The efflux assay, described by Venglarik, C. J. et al., *Am. J. Physiol.* 259, C358-C364, (1990 provides a qualitative estimate of agonist-stimulated Cl conductance pathways in Cl-secreting epithelia, as judged from the inhibitory effects of Cl channel blockers and depolarizing membrane potentials on $^{125}I$ efflux. FIG. 3A shows the time-course of the $^{125}I$ efflux rate constant (r) in two clones, pLJ 6 and pLJ-CFTR 6, with and without the addition of forskolin, an agent which stimulates adenylate cyclase. Following a basal efflux period in the absence of agonist, forskolin increased $^{125}I$ efflux rate from pLJ-CFTR clone 6 from 0.32 to 0.70 $min^{-1}$; pLJ 6 did not respond. r values obtained before forskolin addition and during the peak of the forskolin response provided an estimate of the relative stimulation of $^{125}I$ efflux (i.e. $r_{forsk}/r_{basal}$). In the responding pLJ-CFTR clones, the peak forskolin effect on anion efflux was observed during the first three flux periods following forskolin addition (15-45 sec).

Figure 1B:
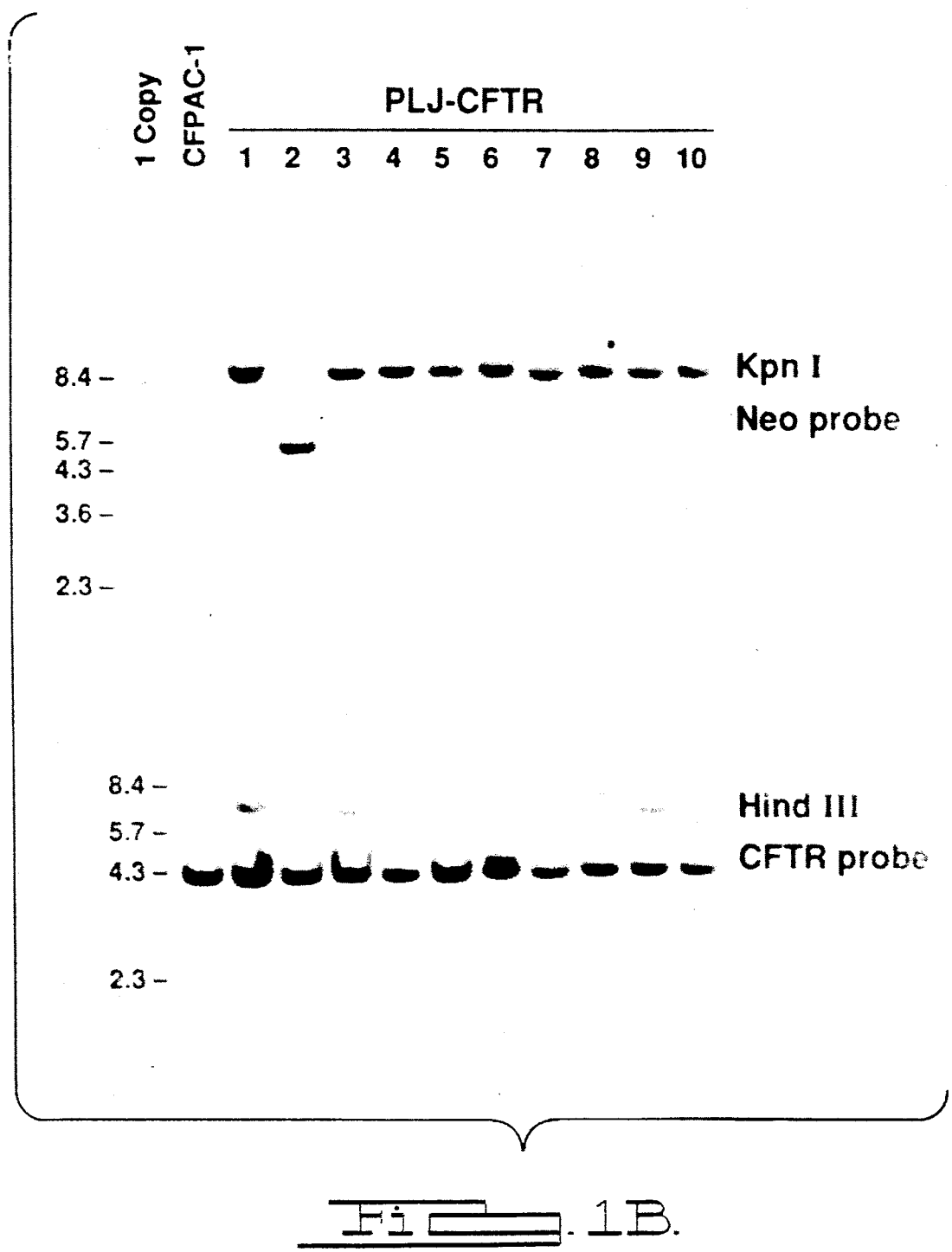
FIG. 1B shows the results of gel blot hybridization of Kpn I-restricted DNA using a Neo specific probe (tope panel) and Hind III digested DNA using an exon 13 CFTR specific probe (bottom panel). CFPAC-1 cells were infected with pLJ or pLJ-CFTR virus and selected in the presence of G418 in order to isolate individual clones. High molecular weight DNA was isolated from each clone and analyzed by the method of gel blot hydridization. In the top panel, DNA was digested with Kpn I and the filter was hybridized to a Neo specific probe, whereas in the bottom panel, DNA was digested with Hind III and the filter was hybridized to the exon 13 CFTR specific probe. The 4.3 kb band in all lanes arises from the endogenous CFTR gene. Samples include: CFPAC-1 DNA (10 $\mu$g); lane "1 copy"-CFPAC-1 DNA (10 $\mu$g) supplemented with 7.5 pg pLJ-CFTR plasmid DNA; lane "CFPAC-1"- CFPAC-1 DNA (10$\mu$g) and lanes "pLG-CFTR 1 through 10"-DNA(10 $\mu$g) from pLJ-CFTR clones 1 through 10. Molecular size standards in dilobases are indicated along the right border.
Figure 3B:
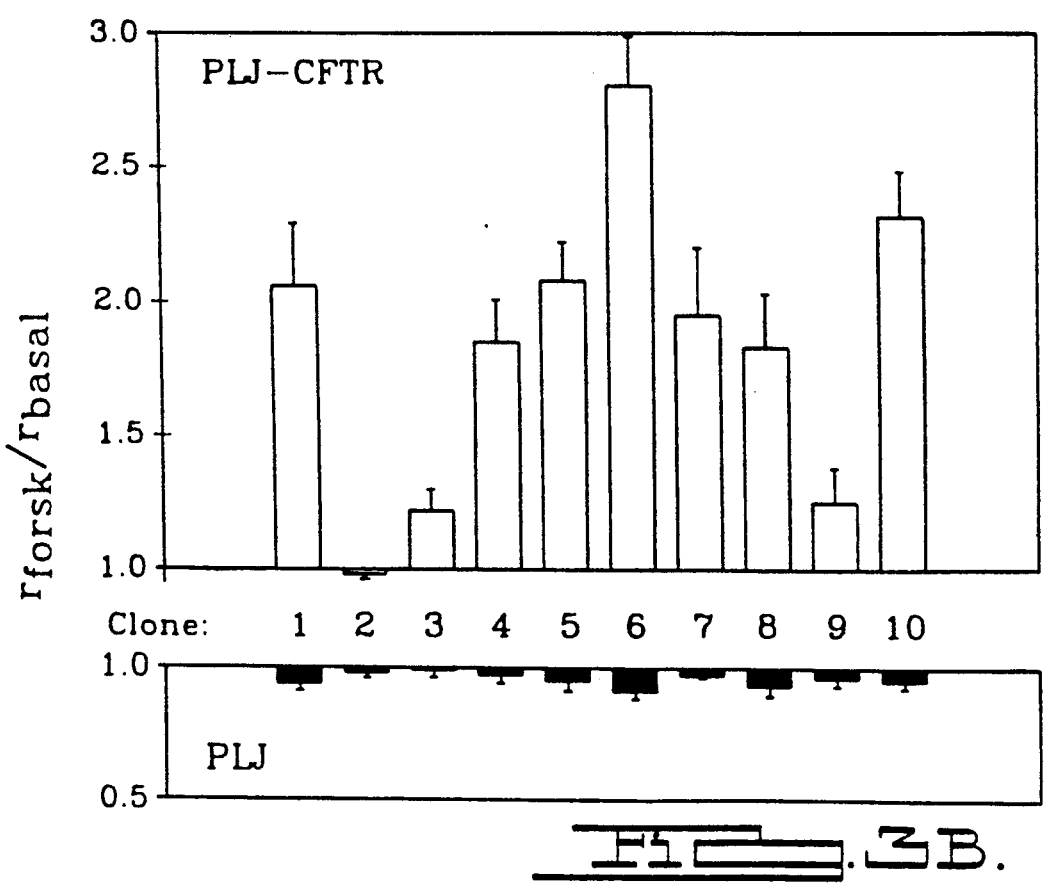
FIG. 3B is a graph illustrating the effect of forskolin on $^{125}$I efflux in PLJ and pLJ-CFTR clones as compared to basal $^{125}$I efflux. Ratio of forskolin-stimulated to basal $^{125}$I efflux in pLJ and pLJ-CFTR clones 1–10, r values were taken before and after forskolin addition. For pLJ-CFTR clone 2, the same scaling applies below 1.0. Values are mean +/−SEM; n=9 for all clones expect pLJ 5 were n=7.

Data derived from twenty clones is illustrated in FIG. 3B. Seven of ten pLJ-CFTR clones shows significant increases in $^{125}I$ efflux in response to forskolin, whereas none (0/10) of the control pLJ clones responded to forskolin. The parent cell line, CFPAC-1, also shows no response to forskolin or cAMP analogues as described by Schoumacher, R. A. et al., *PNAS (USA)* 87, 4012-4016 (1990) pLJ-CFTR clone 2 showed a major deletion in its CFTR cDNA by gel blot hybridization as shown in FIG. 1B, accounting for the failure of forskolin to stimulate $^{125}I$ efflux. In the seven responding pLJ-CFTR clones, the relative stimulation of anion efflux by forskolin ranged from 1.8 to 2.8-fold. This compares well with the 3.5-fold stimulation of efflux reported recently for the colonic tumor cell line T84 by Venglarik, supra. Our results indicate that expression of CFTR cDNA endows CFPAC-1 cells with cAMP-responsive anion efflux.

The correlation between forskolin responsiveness of the pLJ-CFTR clones and their CFTR mRNA levels was not striking as illustrated by a comparison of FIGS. 2 and 3B. Three of the best responders in efflux assay showed high mRNA levels (i.e., pLJ-CFTR clones 1, 6 and 10). In other instances, however ,the correlation was not as good. For example, clones 7 and 8 showed approximately a 2-fold response to forskolin but had relatively low mRNA levels, and clones 3 and 9 showed a low forskolin response, despite the presence of readily detectable CFTR mRNA.

Addition of the Ca ionophore, ionomycin, increased $^{125}I$ efflux in all control and CFTR clones. Values of $r_{iono}/r_{basal}$ averaged 14+/−2 in pLJ and 14+/−1 in pLJ-CFTR (n=20) in each group; no significant differences were detected between individual clones. The extent of response of LJ clones to ionomycin is similar to that observed previously in wild-type CFPAC-1 cells by Schoumacher et al., supra (1990), and is about three times the response of T84 cells observed by Venglarik et al., supra. The ability of Ca ionophores and Ca-mediated agonists to stimulate Cl secretion has been reported for airway and sweat gland cells derived from both normal individuals and CF patients. See Sato, K. et al., *J. Clin. Invest.* 73, 1763-1771 (1984); Frizzell et al., supra (1986); Willumsen, N. J. et al., *Am. J. Physiol.* 256, C226-C233 (1989). The presence of this response in CF cells indicates that CFTR is not required for Ca-mediated Cl transport stimulation. The lack of significant differences in the extent of Ca stimulation in pLJ and pLJ-CFTR clones suggest that CFTR does not modulate the activity of Ca-mediated regulatory pathways that govern Cl secretion.

Clones Transduced with the CFTR Retrovirus Show cAMP-Induced Cl Currents

Figure 4A:
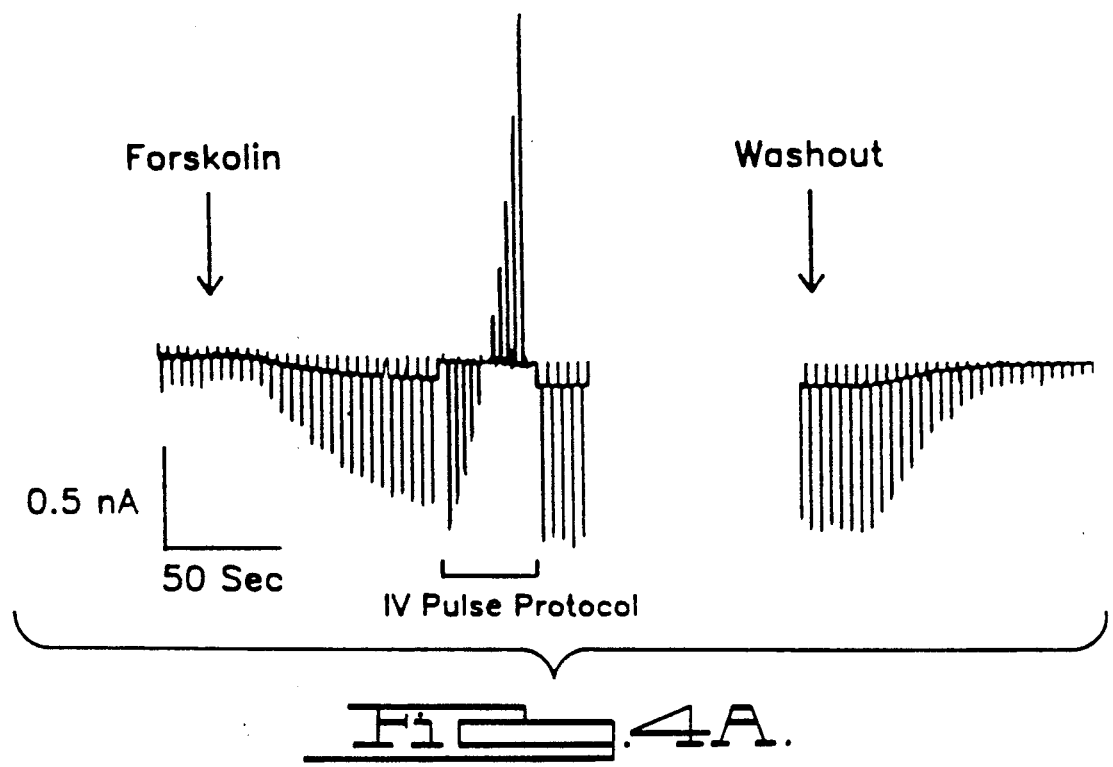
FIG. 4A is a whole-cell voltage clamp record of stimulation of inward currents by forskolin in a pLJ-CFTR clone 1. The stimulation of inward currents in a pLJ-CFTR clone 1 cell by 5 μM forskolin under whole-cell voltage-clamp is shown. Membrane voltage was held at −10 mV and pulsed to 0 and −84 mV. The gap in the record represents time (6 min) during which bath solution substitutions were performed to determine ion selectivity of the forskolin-induced current (see FIG. 3C). Pulse protocols for determining the I-V relations were run at indicated times. Similar results were obtained in 11 pLJ-CFTR clone 1, 6 and 10 cells.
Figure 4B:
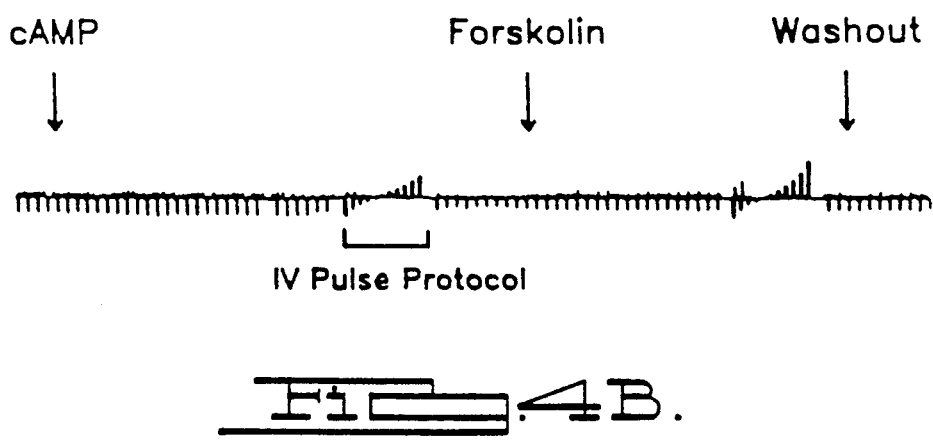
FIG. 4B illustrates the failure of cAMP or forskolin in stimulating membrane currents in a pLJ clone 6 cell. Both cAMP (400 μM) and forskolin (5 μM) failed to stimulate membrane currents in a pLJ clone 6 cell. Membrane voltage was held at −20 mV and pulsed to 0 mV and −84 mV. Similar results were obtained in 5 pLJ clone 6 cells.

Whole-cell path-clamp recordings were used to determine whether the cAMP-induced increase in anion efflux in pLJ-CFTR clones of FIG. 3 was due to stimulation of Cl conductance pathways as described in Cliff, W. H. et al., *PNAS (USA)* 87, 4956-4960 (1990). A typical response of pLJ-CFTR clone 1 is illustrated in FIG. 4A. Chloride currents were measured as the inward current produced by voltage pulses to −84 mV. Similar increases in inward current were observed in 11 of 13 cells from pLJ-CFTR clones 1, 6, and 10 in which addition of forskolin (5 μM) or cAMP (200 to 800 μM) increased inward currents from 220 +/−68 pA to 1690 +/−495 pA in responding cells. The magnitude of this response compares favorably with that observed in T84 cells by Cliff et al., supra. As shown in FIG. 4B, no current responses were observed in cells from the control cone, PLJ 6 (n=6). As observed from the $^{125}I$ efflux determinations, ionomycin (2 μM) increased inward currents in both pLJ (n=4) and pLJ-CFTR (n=3) clones.

FIG. 4C illustrates current-voltage (I-V) relations of the forskolin-stimulated current obtained form pLJ-CFTR clone 1. The I-V relation of the stimulated current appeared to be linear, as observed in T84 cells by Cliff et al., supra. Currents were determined using equal bath and pipette Cl concentrations reversed near the Cl equilibrium potential of 0 mV. Reducing bath Cl to 6 mM (glutamate replacement) decreased the outward currents and shifted the reversal potential for current flow to +66 mV, a value close to the Cl equilibrium potential (+80 mV) for this outwardly-directed Cl gradient. Replacement of bath Na by N-methyl-D-glucamine (NMDG) did not significantly alter the I-V relation. These finding indicate that the forskolin-stimulated current is Cl-selective, and that the simulation of anion efflux in pLJ-CFTR clones is due to activation of Cl conductance pathways.

EXPERIMENTAL PROCEDURES

The following experimental procedures were employed n the Specific Examples set forth above:

CFPAC-1 cells were maintained in culture as described previously by Schoumacher et al., supra (1990)l; cells used for retroviral infection were at passage 72. Infection populations of CFPAC-1 cells were selected in medium containing G418 (1 mg/ml) in order to isolate individual clones. Transduced CFPAC-1 cells were removed from selection soon after they were expanded as clones. This was not associated with an apparent loss of proviral sequences of proviral expression. The amphotropic packaging cell line ΨCrip, was maintained in Dulbecco's modified Eagle'medium supplemented with 10% calf serum and penicillin/streptomycin as described by Danos, O. et al., *PNAS (USA)* 85, 5460-6464 (1988).

Construction of CFTR cDNA

The cDNA was constructed by joining the overlapping clones 10-1, T16-1 and T16-4.5 as described by Riordan et al., supra. 10-1 and T16-1 were ligated at the unique Nru I site in exon 4 and the resultant construct, spanning exons 1 through 13, joined to T16-4.5. This was done by inserting a Sac I-Eco RI partial digestion product of T16-4.5, extending from exon 13 to exon 24, into the respective sites of the 5' 13-exon construct. These manipulations generated a 4.5 kb clone containing the entire coding sequence as previously described by Riordan et al., supra. It was observed that most clones generated from these construction attempts were grossly rearranged. Upon sequencing of an apparently intact construct, a 57 bp deletion was identified in exon 6b occurring between the two copies of a 13 bp direct repeat. On inspection, this interval was noted to contain a consensus prokaryotic promoter sequence. In an attempt to disrupt the repeat, three single nucleotide alterations were made by in vitro mutagenesis. The introduced changes which do not alter the CFTR translation product and result in a stable construct, include substitution of C for T at position 930, G for A at 933, and C for T at position 936. The modified reconstructed CFTR plasmid is called CFTR 4.6.

The above described changes were accomplished by synthesis of an oligonucleotide which matched the normal sequence except for the presence of G at 933 and C at 936. The antisense strand of this segment of the CFTR cDNA was cloned into single-stranded M13 phage, and mutagenized with the oligonucleotide using standard techniques as described by Smith, M., (1989) *Annu. Re. Genet.*, 19, 423 (1985); Sangrook, J., et al.: Molecular cloning. A Laboratory Manual, 2nd ed., Cold Spring Harbor Press, 15.51-15.80 (1989). The resulting clone, shown in FIG. 5, was sequenced and found to have an additional unexpected base change at position 930, which is also in a silent nucleotide position not altering the encoded protein.

It will also be appreciated that other methods to stabilize the full-length CFTR cDNA can be used in the practice of the invention. Any alteration in the fortuitous *E. coli* promoter in exon 6b, as shown in FIG. 5, which renders it non-functional while preserving the correct amino acid coding sequence for CFTR will accomplish this same goal. For example, mutagenesis of the CATACT sequence underlined in FIG. 5 can be accomplished in several ways which will not alter the amino acid sequence (e.g. CGTATT), but will inactivate the sequence as a prokaryotic promoter, rendering it stable in the usual cloning vectors.

Retroviral Vectors and Recombinant Retroviruses

Digestion of the modified CFTR plasmid with Sac I released the modified CFTR cDNA on a 4.6 kb restriction fragment. The Sac I sites were converted to Bcl I sites with oligonucleotides and the linkered fragment was cloned into the Bam I site of the retroviral vector pLJ previously described by Korman et al., supra. This recombinant vector, called pLJ-CFTR, is presented in FIG. 1A. Retroviral vector pLJ and pLJ-CFTR were transfected into the amphotropic packaging cell line ΨCrip as described. Tissue culture media was removed from plates containing the transfected packaging cells 24 hours later in order to harvest the transiently produced amphotropic virus.

CFPAC-1 cells, passaged 1:5 onto 10 cm$^2$ plates, were exposed to viral supernatants supplemented with polybrene (4μg/ml) for 12 to 16 hours. When the cells reached confluence, they were passaged 1:10 into medium containing G418 (1 mg/ml). Clones of cells were isolated, expanded, and cryopreserved.

DNA and RNA Analysis of CFPAC-1 Clones

High molecular weight DNA was isolated form CFPAC-1 cells as described and analyzed by gel blot hybridization as described by Wilson et al., supra (1988). Total cellular RNA was purified and subjected to RNA blot analysis of Wilson et al. supra (1988). Filters were hybridized with a variety of DNA probes that were labeled to a high specific activity using the random priming method of Feinberg, A. P. et al., *Anal. Biochem.* 132, 6-13 (1983). These probes include: 1) Exon 13 of CFTR isolated following PCR amplification of cloned cDNA using oligonucleotides that flank the borders of this exon, (NT 1900 to 2611); 2) Neo-specific sequences on a 960 base pair Hind III to Nco I fragment of pSV2Neo, and 3) human γ actin cDCNA.

Anion Efflux Measurements

Radioisotopic anion efflux was determined as described by Venglarik et al., supra. Briefly, cell monolayers were preloaded with $^{125}$I for 30 min; after two washes, efflux was monitored at 15 sec intervals using a sample-replace procedure. At the end of the experiment, tracer remaining in the cell monolayer was extracted with 0.1 N HPO$_3$. The efflux rate constant (r) for each sampling interval was calculated as follows: $r = [\ln(R_1) - \ln(R_2)]/(t_1 - t_2)$, where $R_1$ and $R_2$ are the percent of loaded $^{125}$I remaining in the monolayer at times (t) 1 and 2. Forskolin or ionomycin were added after the fifth 15-sec sampling interval. The degree of agonist stimulation is expressed as $\gamma_{agonist}/\gamma_{basal}$ where $\gamma_{agonist}$ is the maximal value observed in the presence of agonist an $\gamma_{basal}$ is taken from flux interval immediately prior to agonist addition.

Most of the extracellular $^{125}$I washout occurs during the initial 60 sec of sampling as set forth by Venglarik et al., supra; this period was ignored in the rate constant calculations. However, a small residual efflux from the extracellular space after 60 sec leads to a slight underestimate of the agonist response because the extracellular compartment washes out faster than the cellular compartment. Therefore, when there is no efflux response to forskolin, r determined immediately after forskolin addition is slightly less than that measured before forskolin is added. This accounts for the finding that $\gamma_{frosk}/\gamma_{basal}$ is between 0.9 and 1.0 in the pLJ clones shown in FIG. 3B.

Whole-Cell Current Recordings

Macroscopic currents were recorded during whole-cell patch-clamp by methods previously described by Cliff et al., supra. Recordings were made at 37° C. with the following solutions (mM); bath: 115 NaCl, 40 N-methyl-D-glucamine (NMDG)-glutamate, 5 K-glutamate, 2 MgCl$_2$, 1 CaCl$_2$, 10 HEPES (pH 7.2); pipette: 115 KCl, 35 NMDG-glutamate, 0.25 EGTA, 0.09 CaCl$_2$ (100 nM free Ca), 2 MgCl$_2$, 2 Na$_2$ATP, 0.20 Na$_2$GTP, 10 HEPES (pH 7.2). Membrane potentials were clamped alternately for 500 msec duration of three voltages, two of which were chosen to equal the equilibrium potentials for Cl (0 mV) and K (−84 mV). This permits the Cl and K currents to be monitored during agonist responses as described by Cliff et al., supra. Pulsing was interrupted to determine current-voltage relations by stepping the clamp voltage between +/−100 mV at 20 mV increments as shown in FIG. 4C.

SPECIFIC EXAMPLES - II

Retrovirus-Mediated Transduction of Pancreatic and Pulmonary Epithelial Cells Retrovirus-mediated gene transduction into various epithelial cells was optimized using a replication defective retrovirus that expresses the $\beta$-galactosidase gene form E.coli. This was used because expression of viral directed $\beta$-galactosidase can be detected in situ using cytochemical reaction that stains the transduced cell blue. The amphotropic virus producer cell line made form the $\beta$-galactosidase expressing BAG vector, which has been described previously, was used as a source of virus. This virus producing cell line is called BAG5. The supernatant over a confluent plate of BAG5 cells were harvested, filtered, and used to infect various epithelial cells as described below.

Pancreatic Epithelial Cell Line

CFPAC-1 is a cell line derived from an adenocarcinoma of a patient with CF which expresses the cellular defect characteristic of CF (i.e. chloride channels are not activated in the presence of cAMP agonists). CFPAC-1 cells were split at various dilutions (1:2, 1:15, 1:10, and 1:20) and 24 hours later exposed to fresh virus supernatants that had been supplemented with polybrene (4µg/ml). Twelve hours later the virus was replaced with fresh medium. When confluent, the cells were analyzed for the expression of viral directed $\beta$-galactosidase as described. Optimal infection efficiency was obtained with CFPAC-1 cells that were split 1 to 5 the day before infection. Under optimal conditions, a single exposure to virus led to stable transduction of the $\beta$-galactosidase gene into 30–40% of the cells. Expression of $\beta$-galactosidase has been stable in cultured cells for over 2 months. Attempts to reinfect CFPAC-1 cells on subsequent days led to little augmentation of infection efficiency.

Airway Epithelial Cells

As discussed previously, airway epithelial cells are the most desirable targets for gene transfer because the pulmonary complications of CF are usually its most morbid and life-limiting. Taussig, supra (1984). Since airway epithelial cells are easily infected with recombinant retroviruses, the gene transfer approaches described in the preceding and following examples will also be useful for gene therapies directed to airway epithelial cells such as those of the lung.

An epithelial cell line derived form an airway of a patient with CFR was used as a potential target for retrovirus-mediated gene transfer. These cells had been described previously and have been called T43 cells. Freshly harvested BAG5 virus was supplemented with polybrene and exposed to T43 cells that had been split 1:5, 24 hours previously. Cells were exposed to virus for 12–18 hours and allowed to grow to confluence before being analyzed for viral directed $\beta$-galactosidase expression using the previously described cytochemical assay. Under optimal conditions, greater than 25% of CFPAC cells were stably transduced with the $\beta$-galactosidase gene after a single exposure to virus.

Direct Delivery of CFTR Expressing Vectors to the Airway Epithelial Cells

One approach to the use of recombinant retroviruses and the treatment of CF is to introduce a functional CFTR gene into epithilial cells in vivo by directly delivering retroviruses into the airway. Several approaches can be taken for the direct delivery of retroviruses. The more invasive approach would be to intubate the patient and lavage the airway with concentrated solutions of CFTR expressing retrovirus. Stable retroviral expression requires that the provirus integrates into chromosomal DNA. This occurs most efficiently if the recipient cells are dividing. It may be necessary to stimulate regeneration of the epithelial soon after exposure to virus. This could be accomplished with mechanical or chemical irritation of the airway.

The less morbid approach would be to deliver the normal CFTR gene to airway epithelial cells in vivo by a nebulized preparation that can be inhaled. Many different pharmacologic agents are efficiently delivered to a large surface of the airway by nebulized treatments. It is possible that the beneficial effect achieved by this method may be transient. It may, therefore, be necessary to give repeated doses of the drug. The gene delivery system used for direct gene introduction may not have to be viral based. Direct inhalation of DNA protein complexes or DNA expression vectors in liposomes may be a safer and more effective gene delivery system than retroviruses.

Transplantation of Genetically Modified Airway Epithelial Cells

This approach to somatic gene therapy of CF is similar in concept to bone marrow directed gene therapy. We would propose to isolate airway epithelial cells from the CF patient, establish cultures of the cells, sued recombinant retroviruses described in this invention to stably correct the defect in the cells, and transplant the genetically modified cells into the patient so they can repopulate the airway. In order to achieve efficient repopulation in the airway with genetically modified cells, it may be necessary to perturb the integrity of the endogenous epithelial lining through mechanical or chemical irritation.

alternative Gene Transfer Delivery Systems

Other gene deliveries systems for genetic correction of CF defects also fall within the scope of the present invention. For these experiments plasmid-based DNA vectors will be used. An example of such a vector is presented in FIG. 6. This is a simple transfection-based vector in which transcription is initiated from actin flanking systems and terminated from heterologous 3' polyadenylation $\beta$sequences.

The vector was constructed in the following manner. The backbone contained sequences from PC18 (nucleotide 6928 to 4553) and 5' flanking region of the chicken $\beta$actin gene (nucleotide 6928 to 7754) and 3' flanking sequences of Bovine growth hormone polyadenylation signal (nucleotide 4827 to 4553). The full length CFTR sequences spanning the entire coding region, and containing the three nucleotide changes discussed earlier, were removed from the vector CFTR on a Sac I to Sal I fragment, and cloned into the vector backbone described above.

It will be appreciated by those skilled in the art that this vector could be used in several gene delivery system.

Lipofection

The previously described procedure is based on the encapsidation of DNA liposomes. When cells are incubated with liposomes, they take up the DNA and express it. We proposed to dilute DNA of an expression vector and lipid (DOTMA) to 1.5 ml in Hepes buffered slane and mix these constituents to form lipid-DNA complexes. Liposomes could then be used to transfected airway cells in vivo by lavaging an intubated patient with liposome containing solution or by administering the liposomes by inhalation.

DNA-Protein Complexes

An alternative approach to targeted gene delivery is through the formation of a DNA protein complex. This type of gene transfer substrate is constructed in the following manner. A polypeptide ligand for a receptor on a respiratory epithelial cell is conjugated to polylysine with ethylidene diamino carbodiimide as described. This protein conjugate is complexed to DNA of a transfection vector by mixing equal mass quantities of protein conjugate and DNA in 0.25 molar sodium chloride. The DNA/protein complex is taken up by respiratory airway cells and the gene is expressed. This could be used to directly deliver the CFTR gene to airway epithelial cells in vivo using the approaches described for liposomes.

It is apparent that many modifications and variations of this invention as set forth as may be made without departing from the spirit and scope thereof. The specific embodiments described herein are given by way of example only and the invention is limited only by the terms of the appended claims.

SEQUENCE LISTING

```
                    ↓↓
AAT TGG AAG CAA ATG ACA TCA CAG CAG GTC AGA GAA AAA GGG TTG  45

AGC GGC AGG CAC CCA GAG TAG TAG GTC TTT GGC ATT AGG AGC TTG  90

AGC CCA GAC GGC CCT AGC AGG GAC CCC AGC GCC CGA GAG ACC ATG 135
                                                         M

CAG AGG TCG CCT CTG GAA AAG GCC AGC GTT GTC TCC AAA CTT TTT 180
 Q   R   S   P   L   E   K   A   S   V   V   S   K   L   F

TTC AGC TGG ACC AGA CCA ATT TTG AGG AAA GGA TAC AGA CAG CGC 225
 F   S   W   T   R   P   I   L   R   K   G   Y   R   Q   R

CTG GAA TTG TCA GAC ATA TAC CAA ATC CCT TCT GTT GAT TCT GCT 270
 L   E   L   S   D   I   Y   Q   I   P   S   V   D   S   A

*
GAC AAT CTA TCT GAA AAA TTG GAA AGA GAA TGG GAT AGA GAG CTG 315
 D   N   L   S   E   K   L   E   R   E   W   D   R   E   L

*
GCT TCA AAG AAA AAT CCT AAA CTC ATT AAT GCC CTT CGG CGA TGT 360
 A   S   K   K   N   P   K   L   I   N   A   L   R   R   C

TTT TTC TGG AGA TTT ATG TTC TAT GGA ATC TTT TTA TAT TTA GGG 405
 F   F   W   R   F   M   F   Y   G   8   F   L   Y   L   G

GAA GTC ACC AAA GCA GTA CAG CCT CTC TTA CTG GGA AGA ATC ATA 450
 E   V   T   K   A   V   Q   P   L   L   L   G   R   I   I

GCT TCC TAT GAC CCG GAT AAC AAG GAG GAA CGC TCT ATC GCG ATT 495
 A   S   Y   D   P   D   N   K   E   E   R   S   I   A   I

TAT CTA GGC ATA GGC TTA TGC CTT CTC TTT ATT GTG AGG ACA CTG 540
 Y   L   G   I   G   L   C   L   L   F   I   V   R   T   L

CTC CTA CAC CCA GCC ATT TTT GGC CTT CAT CAC ATT GGA ATG CAG 585
 L   L   H   P   A   I   F   G   L   H   H   I   G   M   Q

*
ATG AGA ATA GCT ATG TTT AGT TTG ATT TAT AAG AAG ACT TTA AAG 630
 M   R   I   A   M   F   S   L   I   Y   K   K   T   L   K

*
CTG TCA AGC CGT GTT CTA GAT AAA ATA AGT ATT GGA CAA CTT GTT 675
 L   S   S   R   V   L   D   K   I   S   I   G   Q   L   V

AGT CTC CTT TCC AAC AAC CTG AAC AAA TTT GAT GAA GGA CTT GCA 720
 S   L   L   S   N   N   L   N   K   F   D   E   G   L   A

TTG GCA CAT TTC GTG TGG ATC GCT CCT TTG CAA GTG GCA CTC CTC 765
 L   A   H   F   V   W   I   A   P   L   Q   V   A   L   L
```

-continued
SEQUENCE LISTING

```
ATG GGG CTA ATC TGG GAG TTG TTA CAG GCG TCT GCC TTC TGT GGA 810
 M   G   L   I   W   E   L   L   Q   A   S   A   F   C   G

CTT GGT TTC CTG ATA GTC CTT GCC CTT TTT CAG GCT GGG CTA GGG 855
 L   G   F   L   I   V   L   A   L   F   Q   A   G   L   G

AGA ATG ATG ATG AAG TAC AGA GAT CAG AGA GCT GGG AAG ATC AGT 900
 R   M   M   M   K   Y   R   D   Q   R   A   G   K   I   S

GAA AGA CTT GTG ATT ACC TCA GAA ATG ATT GAA AAT ATC CAA TCT 945
 E   R   L   V   I   T   S   E   M   I   E   N   I   Q   S

GTT AAG GCA TAC TGC TGG GAA GAA GCA ATG GAA AAA ATG ATT GAA 990
 V   K   A   Y   C   W   E   E   A   M   E   K   M   I   E

AAC TTA AGA CAA ACA GAA CTG AAA CTG ACT CGG AAG GCA GCC TAT 1035
 N   L   R   Q   T   E   L   K   L   T   R   K   A   A   Y

GTG AGA TAC TTC AAT AGC TCA GCC TTC TTC TTC TCA GGG TTC TTT 1080
 V   R   Y   F   N   S   S   A   F   F   F   S   G   F   F

GTG GTG TTT TTA TCT GTG CTT CCC TAT GCA CTA ATC AAA GGA ATC 1125
 V   V   F   L   S   V   L   P   Y   A   L   I   K   G   I

ATC CTC CGG AAA ATA TTC ACC ACC ATC TCA TTC TGC ATT GTT CTG 1170
 I   L   R   K   I   F   T   T   I   S   F   C   I   V   L

CGC ATG GCG GTC ACT CGG CAA TTT CCC TGG GCT GTA CAA ACA TGG 1215
 R   M   A   V   T   R   Q   F   P   W   A   V   Q   T   W

TAT GAC TCT CTT GGA GCA ATA AAC AAA ATA CAG GAT TTC TTA CAA 1260
 Y   D   S   L   G   A   I   N   K   I   Q   D   F   L   Q

AAG CAA GAA TAT AAG ACA TTG GAA TAT AAC TTA ACG ACT ACA GAA 1305
 K   Q   E   Y   K   T   L   E   Y   N   L   T   T   T   E

GTA GTG ATG GAG AAT GTA ACA GCC TTC TGG GAG GAG GGA TTT GGG 1350
 V   V   M   E   N   V   T   A   F   W   E   E   G   F   G

GAA TTA TTT GAG AAA GCA AAA CAA AAC AAT AAC AAT AGA AAA ACT 1395
 E   L   F   E   K   A   K   Q   N   N   N   N   R   K   T

TCT AAT GGT GAT GAC AGC CTC TTC TTC AGT AAT TTC TCA CTT CTT 1440
 S   N   G   D   D   S   L   F   F   S   N   F   S   L   L

GGT ACT CCT GTC CTG AAA GAT ATT AAT TTC AAG ATA GAA AGA GGA 1485
 G   T   P   V   L   K   D   I   N   F   K   I   E   R   G

CAG TTG TTG GCG GTT GCT GGA TCC ACT GGA GCA GGC AAG ACT TCA 1530
 Q   L   L   A   V   A   G   S   T   G   A   G   K   T   S

CTT CTA ATG ATG ATT ATG GGA GAA CTG GAG CCT TCA GAG GGT AAA 1575
 L   L   M   M   I   M   G   E   L   E   P   S   E   G   K

ATT AAG CAC AGT GGA AGA ATT TCA TTC TGT TCT CAG TTT TCC TGG 1620
 I   K   H   S   G   R   I   S   F   C   S   Q   F   S   W

ATT ATG CCT GGC ACC ATT AAA GAA AAT ATC ATC TTT GGT GTT TCC 1665
 I   M   P   G   T   I   K   E   N   I   I   F   G   V   S

TAT GAT GAA TAT AGA TAC AGA AGC GTC ATC AAA GCA TGC CAA CTA 1710
 Y   D   E   Y   R   Y   R   S   V   I   K   A   C   Q   L

GAA GAG GAC ATC TCC AAG TTT GCA GAG AAA GAC AAT ATA GTT CTT 1755
 E   E   D   I   S   K   F   A   E   K   D   N   I   V   L

GGA GAA GGT GGA ATC ACA CTG AGT GGA GGT CAA CGA GCA AGA ATT 1800
 G   E   G   G   I   T   L   S   G   G   Q   R   A   R   I

TCT TTA GCA AGA GCA GTA TAC AAA GAT GCT GAT TTG TAT TTA TTA 1845
 S   L   A   R   A   V   Y   K   D   A   D   L   Y   L   L
```

-continued
SEQUENCE LISTING

```
GAC TCT CCT TTT GGA TAC CTA GAT GTT TTA ACA GAA AAA GAA ATA  1890
 D   S   P   F   G   Y   L   D   V   L   T   E   K   E   I

TTT GAA AGC TGT GTC TGT AAA CTG ATG GCT AAC AAA ACT AGG ATT  1935
 F   E   S   C   V   C   K   L   M   A   N   K   T   R   I

TTG GTC ACT TCT AAA ATG GAA CAT TTA AAG AAA GCT GAC AAA ATA  1980
 L   V   T   S   K   M   E   H   L   K   K   A   D   K   I

TTA ATT TTG AAT GAA GGT AGC AGC TAT TTT TAT GGG ACA TTT TCA  2025
 L   I   L   N   E   G   S   S   Y   F   Y   G   T   F   S

GAA CTC CAA AAT CTA CAG CCA GAC TTT AGC TCA AAA CTC ATG GGA  2070
 E   L   Q   N   L   Q   P   D   F   S   S   K   L   M   G

TGT GAT TCT TTC GAC CAA TTT AGT GCA GAA AGA AGA AAT TCA ATC  2115
 C   D   S   F   D   Q   F   S   A   E   R   R   N   S   I

CTA ACT GAG ACC TTA CAC CGT TTC TCA TTA GAA GGA GAT GCT CCT  2160
 L   T   E   T   L   H   R   F   S   L   E   G   D   A   P

GTC TCC TGG ACA GAA ACA AAA AAA CAA TCT TTT AAA CAG ACT GGA  2205
 V   S   W   T   E   T   K   K   Q   S   F   K   Q   T   G

GAG TTT GGG GAA AAA AGG AAG AAT TCT ATT CTC AAT CCA ATC AAC  2250
 E   F   G   E   K   R   K   N   S   I   L   N   P   I   N

TCT ATA CGA AAA TTT TCC ATT GTG CAA AAG ACT CCC TTA CAA ATG  2295
 S   I   R   K   F   S   I   V   Q   K   T   P   L   Q   M

AAT GGC ATC GAA GAG GAT TCT GAT GAG CCT TTA GAG AGA AGG CTG  2340
 N   G   I   E   E   D   S   D   E   P   L   E   R   R   L

TCC TTA GTA CCA GAT TCT GAG CAG GGA GAG GCG ATA CTG CCT CGC  2385
 S   L   V   P   D   S   E   Q   G   E   A   I   L   P   R

ATC AGC GTG ATC AGC ACT GGC CCC ACG CTT CAG GCA CGA AGG AGG  2430
 I   S   V   I   S   T   G   P   T   L   Q   A   R   R   R

CAG TCT GTC CTG AAC CTG ATG ACA CAC TCA GTT AAC CAA GGT CAG  2475
 Q   S   V   L   N   L   M   T   H   S   V   N   Q   G   Q

AAC ATT CAC CGA AAG ACA ACA GCA TCC ACA CGA AAA GTG TCA CTG  2520
 N   I   H   R   K   T   T   A   S   T   R   K   V   S   L

GCC CCT CAG GCA AAC TTG ACT GAA CTG GAT ATA TAT TCA AGA AGG  2565
 A   P   Q   A   N   L   T   E   L   D   I   Y   S   R   R

TTA TCT CAA GAA ACT GGC TTG GAA ATA AGT GAA GAA ATT AAC GAA  2610
 L   S   Q   E   T   G   L   E   I   S   E   E   I   N   E

GAA GAC TTA AAG GAG TGC CTT TTT GAT GAT ATG GAG AGC ATA CCA  2655
 E   D   L   K   E   C   L   F   D   D   M   E   S   I   P

GCA GTG ACT ACA TGG AAC ACA TAC CTT CGA TAT ATT ACT GTC CAC  2700
 A   V   T   T   W   N   T   Y   L   R   Y   I   T   V   H

AAG AGC TTA ATT TTT GTG CTA ATT TGG TGC TTA GTA ATT TTT CTG  2745
 K   S   L   I   F   V   L   I   W   C   L   V   I   F   L

GCA GAG GTG GCT GCT TCT TTG GTT GTG CTG TGG CTC CTT GGA AAC  2790
 A   E   V   A   A   S   L   V   V   L   W   L   L   G   N

ACT CCT CTT CAA GAC AAA GGG AAT AGT ACT CAT AGT AGA AAT AAC  2835
 T   P   L   Q   D   K   G   N   S   T   H   S   R   N   N

AGC TAT GCA GTG ATT ATC ACC AGC ACC AGT TCG TAT TAT GTG TTT  2880
 S   Y   A   V   I   I   T   S   T   S   S   Y   Y   V   F
```

```
TAC ATT TAC GTG GGA GTA GCC GAC ACT TTG CTT GCT ATG GGA TTC 2925
 Y   I   Y   V   G   V   A   D   T   L   L   A   M   G   F

TTC AGA GGT CTA CCA CTG GTG CAT ACT CTA ATC ACA GTG TCG AAA 2970
 F   R   G   L   P   L   V   H   T   L   I   T   V   S   K

ATT TTA CAC CAC AAA ATG TTA CAT TCT GTT CTT CAA GCA CCT ATG 3015
 I   L   H   H   K   M   L   H   S   V   L   Q   A   P   M

TCA ACC CTC AAC ACG TTG AAA GCA GGT GGG ATT CTT AAT AGA TTC 3060
 S   T   L   N   T   L   K   A   G   G   I   L   N   R   F

TCC AAA GAT ATA GCA ATT TTG GAT GAC CTT CTG CCT CTT ACC ATA 3105
 S   K   D   I   A   I   L   D   D   L   L   P   L   T   I

TTT GAC TTC ATC CAG TTG TTA TTA ATT GTG ATT GGA GCT ATA GCA 3150
 F   D   F   I   Q   L   L   L   I   V   I   G   A   I   A

GTT GTC GCA GTT TTA CAA CCC TAC ATC TTT GTT GCA ACA GTG CCA 3195
 V   V   A   V   L   Q   P   Y   I   F   V   A   T   V   P

GTG ATA GTG GCT TTT ATT ATG TTG AGA GCA TAT TTC CTC CAA ACC 3240
 V   I   V   A   F   I   M   L   R   A   Y   F   L   Q   T

TCA CAG CAA CTC AAA CAA CTG GAA TCT GAA GGC AGG AGT CCA ATT 3285
 S   Q   Q   L   K   Q   L   E   S   E   G   R   S   P   I

TTC ACT CAT CTT GTT ACA AGC TTA AAA GGA CTA TGG ACA CTT CGT 3330
 F   T   H   L   V   T   S   L   K   G   L   W   T   L   R

GCC TTC GGA CGG CAG CCT TAC TTT GAA ACT CTG TTC CAC AAA GCT 3375
 A   F   G   R   Q   P   Y   F   E   T   L   F   H   K   A

CTG AAT TTA CAT ACT GCC AAC TGG TTC TTG TAC CTG TCA ACA CTG 3420
 L   N   L   H   T   A   N   W   F   L   Y   L   S   T   L

CGC TGG TTC CAA ATG AGA ATA GAA ATG ATT TTT GTC ATC TTC TTC 3465
 R   W   F   Q   M   R   I   E   M   I   F   V   I   F   F

ATT GCT GTT ACC TTC ATT TCC ATT TTA ACA ACA GGA GAA GGA GAA 3510
 I   A   V   T   F   I   S   I   L   T   T   G   E   G   E

GGA AGA GTT GGT ATT ATC CTG ACT TTA GCC ATG AAT ATC ATG AGT 3555
 G   R   V   G   I   I   L   T   L   A   M   N   I   M   S

ACA TTG CAG TGG GCT GTA AAC TCC AGC ATA GAT GTG GAT AGC TTG 3600
 T   L   Q   W   A   V   N   S   S   I   D   V   D   S   L

ATG CGA TCT GTG AGC CGA GTC TTT AAG TTC ATT GAC ATG CCA ACA 3645
 M   R   S   V   S   R   V   F   K   F   I   D   M   P   T

GAA GGT AAA CCT ACC AAG TCA ACC AAA CCA TAC AAG AAT GGC CAA 3690
 E   G   K   P   T   K   S   T   K   P   Y   K   N   G   Q

CTC TCG AAA GTT ATG ATT ATT GAG AAT TCA CAC GTG AAG AAA GAT 3735
 L   S   K   V   M   I   I   E   N   S   H   V   K   K   D

GAC ATC TGG CCC TCA GGG GGC CAA ATG ACT GTC AAA GAT CTC ACA 3780
 D   I   W   P   S   G   G   Q   M   T   V   K   D   L   T

GCA AAA TAC ACA GAA GGT GGA AAT GCC ATA TTA GAG AAC ATT TCC 3825
 A   K   Y   T   E   G   G   N   A   I   L   E   N   I   S

TTC TCA ATA AGT CCT GGC CAG AGG GTG GGC CTC TTG GGA AGA ACT 3870
 F   S   I   S   P   G   Q   R   V   G   L   L   G   R   T

GGA TCA GGG AAG AGT ACT TTG TTA TCA GCT TTT TTG AGA CTA CTG 3915
 G   S   G   K   S   T   L   L   S   A   F   L   R   L   L

AAC ACT GAA GGA GAA ATC CAG ATC GAT GGT GTG TCT TGG GAT TCA 3960
 N   T   E   G   E   I   Q   I   D   G   V   S   W   D   S

ATA ACT TTG CAA CAG TGG AGG AAA GCC TTT GGA GTG ATA CCA CAG 4005
 I   T   L   Q   Q   W   R   K   A   F   G   V   I   P   Q
```

SEQUENCE LISTING

```
AAA GTA TTT ATT TTT TCT GGA ACA TTT AGA AAA AAC TTG GAT CCC  4050
 K   V   F   I   F   S   G   T   F   R   K   N   L   D   P

TAT GAA CAG TGG AGT GAT CAA GAA ATA TGG AAA GTT GCA GAT GAG  4095
 Y   E   Q   W   S   D   Q   E   I   W   K   V   A   D   E

GTT GGG CTC AGA TCT GTG ATA GAA CAG TTT CCT GGG AAG CTT GAC  4140
 V   G   L   R   S   V   I   E   Q   F   P   G   K   L   D

TTT GTC CTT GTG GAT GGG GGC TGT GTC CTA AGC CAT GGC CAC AAG  4185
 F   V   L   V   D   G   G   C   V   L   S   H   G   H   K

CAG TTG ATG TGC TTG GCT AGA TCT GTT CTC AGT AAG GCG AAG ATC  4230
 Q   L   M   C   L   A   R   S   V   L   S   K   A   K   I

TTG CTG CTT GAT GAA CCC AGT GCT CAT TTG GAT CCA GTA ACA TAC  4275
 L   L   L   D   E   P   S   A   H   L   D   P   V   T   Y

CAA ATA ATT AGA AGA ACT CTA AAA CAA GCA TTT GCT GAT TGC ACA  4320
 Q   I   I   R   R   T   L   K   Q   A   F   A   D   C   T

GTA ATT CTC TGT GAA CAC AGG ATA GAA GCA ATG CTG GAA TGC CAA  4365
 V   I   L   C   E   H   R   I   E   A   M   L   E   C   Q
CAA TTT TTG GTC ATA GAA GAG AAC AAA GTG CGG CAG TAC GAT TCC  4410
 Q   F   L   V   I   E   E   N   K   V   R   Q   Y   D   S

ATC CAG AAA CTG CTG AAC GAG AGG AGC CTC TTC CGG CAA GCC ATC  4455
 I   Q   K   L   L   N   E   R   S   L   F   R   Q   A   I

AGC CCC TCC GAC AGG GTG AAG CTC TTT CCC CAC CGG AAC TCA AGC  4500
 S   P   S   D   R   V   K   L   F   P   H   R   N   S   S

AAG TGC AAG TCT AAG CCC CAG ATT GCT GCT CTG AAA GAG GAG ACA  4545
 K   C   K   S   K   P   Q   I   A   A   L   K   E   E   T

GAA GAA GAG GTG CAA GAT ACA AGG CTT TAGAGAGCAGCATAAATG       4590
 E   E   E   V   Q   D   T   R   L

TTGACATGGGACATTTGCTCATGGAATTGGAGCTCGTGGGACAGT  4635
CACCTCATGGAATTGGAGCTCGTGGAACAGTTACCTCTGCCTCAG  4680
AAAACAAGGATGAATTAAGTTTTTTTTTAAAAAAGAAACATTTGG  4725
TAAGGGGAATTGAGGACACTGATATGGGTCTTGATAAATGGCTTC  4770
CTGGCAATAGTCAAATTGTGTGAAAGGTACTTCAAATCCTTGAAG  4815
ATTTACCACTTGTGTTTTGCAAGCCAGATTTTCCTGAAAACCCTT  4860
GCCATGTGCTAGTAATTGGAAAGGCAGCTCTAAATGTCAATCAGC  4905
CTAGTTGATCAGCTTATTGTCTAGTGAAACTCGTTAATTTGTAGT  4950
GTTGGAGAAGAACTGAAATCATACTTCTTAGGGTTATGATTAAGT  4995
AATGATAACTGGAAACTTCAGCGGTTTATATAAGCTTGTATTCCT  5040
TTTTCTCTCCTCTCCCCATGATGTTTAGAAACACAACTATATTGT  5085
TTGCTAAGCATTCCAACTATCTCATTTCCAAGCAAGTATTAGAAT  5130
ACCACAGGAACCACAAGACTGCACATCAAAATATGCCCCATTCAA  5175
CATCTAGTGAGCAGTCAGGAAAGAGAACTTCCAGATCCTGGAAAT  5220
CAGGGTTAGTATTGTCCAGGTCTACCAAAAATCTCAATATTTCAG  5265
ATAATCACAATACATCCCTTAACTGGGAAGGGCTGTTATAATCT   5310
TTCACAGGGGACAGGATGGTTCCCTTGATGAAGAAGTTGATATGC  5355
CTTTTCCCAACTCCAGAAAGTGACAAGCTCACAGACCTTTGAACT  5400
AGAGTTTAGCTGGAAAAGTATGTTAGTGCAAATTGTCACAGGACA  5445
```

-continued
SEQUENCE LISTING

```
GCCCTTCTTTCCACAGAAGCTCCAGGTAGAGGGTGTGTAAGTAGA   5490
TAGGCCATGGGCACTGTGGGTAGACACACATGAAGTCCAAGCATT   5535
TAGATGTATAGGTTGATGGTGGTATGTTTTCAGGCTAGATGTATG   5580
TACTTCATGCTGTCTACACTAAGAGAGAATGAGAGACACACTGAA   5625
GAAGCACCAATCATGAATTAGTTTTATATGCTTCTGTTTTATAAT   5670
TTTGTGAAGCAAAATTTTTTCTCTAGGAAATATTTATTTTAATAA   5715
TGTTTCAAACATATATTACAATGCTGTATTTTAAAAGAATGATTA   5760
TGAATTACATTTGTATAAAATAATTTTTATATTTGAAATATTGAC   5805
TTTTTATGGCACTAGTATTTTTATGAAATATTATGTTAAAACTGG   5850
GACAGGGGAGAACCTAGGGTGATATTAACCAGGGGCCATGAATCA   5895
CCTTTTGGTCTGGAGGGAAGCCTTGGGGCTGATCGAGTTGTTGCC   5940
CACAGCTGTATGATTCCCAGCCAGACACAGCCTCTTAGATGCAGT   5985
TCTGAAGAAGATGGTACCACCAGTCTGACTGTTTCCATCAAGGGT   6030
ACACTGCCTTCTCAACTCCAAACTGACTCTTAAGAAGACTGCATT   6075
ATATTTATTACTGTAAGAAAATATCACTTGTCAATAAAATCCATA   6120
CATTTGTGTAAAAAAAAAAAAAAAAA
```

We claim:

1. A recombinant viral vector for treating a defect in the gene for cystic fibrosis transmembrane regulator in a target cell, the vector comprising:
   a) the DNA of or corresponding to at least a portion of the genome of a virus which portion is cable of infecting the target cells; and
   b) a normal cystic fibrosis transmembrane regulator gene operatively linked to the DNA and capable of expression in the target cell in vivo or in vitro.

2. The recombinant vector of claim 1, wherein the virus is a retrovirus.

3. The recombinant vector of claim 2, wherein the retroviral genome is replication-defective.

4. The recombinant vector of claim 2, further comprising pLJ.

5. The recombinant vector of claim 4, wherein the vector provirus is substantially as shown in FIG. 1A.

6. The recombinant vector of claim 2, wherein the defect being treated causes cystic fibrosis.

7. The recombinant vector of claim 1, wherein the target cell is an epithelial cell.

8. The recombinant vector of claim 6, wherein the epithelial cell is pancreatic.

9. The recombinant vector of claim 6, wherein the epithelial cell is an airway epithelial cell.

10. The recombinant vector of claim 6, wherein the epithelial cell is a cell selected from the group consisting of sweat gland, intestinal, liver and kidney cells.

11. The recombinant vector of claim 7, wherein comprising pLJ.

12. The recombinant vector of claim 8, further comprising pLJ.

13. The recombinant vector of claim 4, wherein the normal cystic fibrosis transmembrane regulation gene includes a silent mutation which stabilizes expression of the gene.

14. A CF cell which expresses a normal cystic fibrosis transmembrane regulator gene introduced therein through retroviral transduction.

15. The cell of claim 14, wherein the cell is derived from a pLJ-cystic fibrosis transmembrane regulator clone.

16. The recombinant vector of claim 13, wherein the silent mutation comprises the presence of cytosine at nucleotide position 930 of the cystic fibrosis transmembrane regulator cDNA sequence, guanine at nucleotide position 933 of the cystic fibrosis transmembrane regulator cDNA sequence, and cytosine at nucleotide position 936 of the cystic fibrosis transmembrane regulator cDNA sequence.

* * * * *